(12) United States Patent
Kalmeta

(10) Patent No.: US 11,730,760 B2
(45) Date of Patent: Aug. 22, 2023

(54) LASER ASSISTED WOUND HEALING PROTOCOL AND SYSTEM

(71) Applicant: BIOREGENTECH, INC., Irvine, CA (US)

(72) Inventor: Margaret Kalmeta, Aptos, CA (US)

(73) Assignee: THE BIOREGENTECH INSTITUTE, INC., Irvine, CA (US)

( * ) Notice: Subject to any disclaimer, the term of this patent is extended or adjusted under 35 U.S.C. 154(b) by 0 days.

(21) Appl. No.: 14/937,858

(22) Filed: Nov. 10, 2015

(65) Prior Publication Data

US 2016/0158284 A1 Jun. 9, 2016

Related U.S. Application Data

(63) Continuation-in-part of application No. 13/864,226, filed on Apr. 16, 2013, now Pat. No. 9,180,319, (Continued)

(51) Int. Cl.
*A61K 33/42* (2006.01)
*A61K 31/198* (2006.01)
(Continued)

(52) U.S. Cl.
CPC ............ *A61K 33/42* (2013.01); *A61C 1/0046* (2013.01); *A61K 8/20* (2013.01); *A61K 8/24* (2013.01);
(Continued)

(58) Field of Classification Search
CPC ... A61C 1/0046; A61C 19/043; A61C 19/063; A61C 1/00; A61C 3/00; A61C 8/00;
(Continued)

(56) References Cited

U.S. PATENT DOCUMENTS 3,950,529 A    4/1976  Fischer et al.
5,002,051 A *  3/1991  Dew ................ A61B 17/00491
                                        128/DIG. 22
(Continued)

FOREIGN PATENT DOCUMENTS

EP      1223924      7/2002
TW      469045 U     1/2014
(Continued)

OTHER PUBLICATIONS

Koort et al., Laser, A combined device for optimal soft tissue applications in laser dentistry, 4, pp. 24-29, Jan. 2013. (Year: 2013).*

(Continued)

*Primary Examiner* — Lezah Roberts
(74) *Attorney, Agent, or Firm* — Pillsbury Winthrop Shaw Pittman LLP

(57) ABSTRACT

A method of treating gum disease while healing the wound in the periodontium using a soft tissue diode laser which generates a beam of light having a wavelength in the visible portion of the electromagnetic spectrum (400 nm-700 nm) at a laser power of 0.001 to 1.2 watts, used with intermittent stops to control tissue temperature and biostimulate the periodontium to regenerate and heal its wound when used with substrates, the method comprising: placing the tip of the laser inside the sulcus; penetrating the entire sulcus by moving the laser light circumferentially around the tooth vertically and horizontally throughout the sulcus with intermittent stops to control tissue temperature and placing substrates in the sulcus prior to blood clot formation; followed by RF treatment of the sulcus by placing the RF headpiece tips perpendicular to the sulcus to receive RF current which further penetrates the wound site.

8 Claims, 23 Drawing Sheets

Related U.S. Application Data which is a continuation-in-part of application No. 13/078,757, filed on Apr. 1, 2011, now abandoned.

(51) Int. Cl.

| | | |
|---|---|---|
| A61K 31/405 | (2006.01) | |
| A61K 31/4172 | (2006.01) | |
| A61K 31/401 | (2006.01) | |
| A61K 31/7076 | (2006.01) | |
| A61K 31/221 | (2006.01) | |
| A61K 31/7072 | (2006.01) | |
| A61K 31/708 | (2006.01) | |
| A61K 31/7068 | (2006.01) | |
| A61K 31/192 | (2006.01) | |
| A61K 33/14 | (2006.01) | |
| A61K 31/7048 | (2006.01) | |
| A61K 31/7004 | (2006.01) | |
| A61K 31/7008 | (2006.01) | |
| A61K 31/07 | (2006.01) | |
| A61K 31/592 | (2006.01) | |
| A61K 31/593 | (2006.01) | |
| A61K 31/355 | (2006.01) | |
| A61K 31/122 | (2006.01) | |
| A61K 31/714 | (2006.01) | |
| A61K 31/575 | (2006.01) | |
| A61K 31/51 | (2006.01) | |
| A61K 31/525 | (2006.01) | |
| A61K 31/455 | (2006.01) | |
| A61K 31/197 | (2006.01) | |
| A61K 31/675 | (2006.01) | |
| A61K 31/4188 | (2006.01) | |
| A61K 31/519 | (2006.01) | |
| A61K 31/375 | (2006.01) | |
| A61K 31/14 | (2006.01) | |
| A61K 33/06 | (2006.01) | |
| A61K 33/00 | (2006.01) | |
| A61K 33/18 | (2006.01) | |
| A61K 33/24 | (2019.01) | |
| A61K 33/38 | (2006.01) | |
| A61K 33/34 | (2006.01) | |
| A61K 33/30 | (2006.01) | |
| A61K 33/04 | (2006.01) | |
| A61K 33/26 | (2006.01) | |
| A61K 33/22 | (2006.01) | |
| A61K 8/368 | (2006.01) | |
| A61K 8/24 | (2006.01) | |
| A61K 8/44 | (2006.01) | |
| A61K 8/20 | (2006.01) | |
| A61K 8/60 | (2006.01) | |
| A61Q 11/00 | (2006.01) | |
| A61N 5/06 | (2006.01) | |
| A61C 1/00 | (2006.01) | |
| A61K 8/41 | (2006.01) | |
| A61K 33/242 | (2019.01) | |
| A61N 5/067 | (2006.01) | |

(52) U.S. Cl.
CPC .............. *A61K 8/368* (2013.01); *A61K 8/416* (2013.01); *A61K 8/44* (2013.01); *A61K 8/442* (2013.01); *A61K 8/606* (2013.01); *A61K 31/07* (2013.01); *A61K 31/122* (2013.01); *A61K 31/14* (2013.01); *A61K 31/192* (2013.01); *A61K 31/197* (2013.01); *A61K 31/198* (2013.01); *A61K 31/221* (2013.01); *A61K 31/355* (2013.01); *A61K 31/375* (2013.01); *A61K 31/401* (2013.01); *A61K 31/405* (2013.01); *A61K 31/4172* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/575* (2013.01); *A61K 31/592* (2013.01); *A61K 31/593* (2013.01); *A61K 31/675* (2013.01); *A61K 31/7004* (2013.01); *A61K 31/7008* (2013.01); *A61K 31/708* (2013.01); *A61K 31/7048* (2013.01); *A61K 31/7068* (2013.01); *A61K 31/7072* (2013.01); *A61K 31/7076* (2013.01); *A61K 31/714* (2013.01); *A61K 33/00* (2013.01); *A61K 33/04* (2013.01); *A61K 33/06* (2013.01); *A61K 33/14* (2013.01); *A61K 33/18* (2013.01); *A61K 33/22* (2013.01); *A61K 33/24* (2013.01); *A61K 33/242* (2019.01); *A61K 33/26* (2013.01); *A61K 33/30* (2013.01); *A61K 33/34* (2013.01); *A61K 33/38* (2013.01); *A61N 5/0603* (2013.01); *A61N 5/0613* (2013.01); *A61Q 11/00* (2013.01); *A61N 5/062* (2013.01); *A61N 5/067* (2021.08); *A61N 5/0624* (2013.01); *A61N 2005/063* (2013.01); *A61N 2005/0606* (2013.01); *A61N 2005/0659* (2013.01); *A61N 2005/0663* (2013.01)

(58) Field of Classification Search
CPC ........ A61C 15/00; A61C 17/00; A61K 33/42; A61K 38/39; A61K 6/00; A61N 2005/0606; A61N 2005/063; A61N 2005/0644; A61N 2005/0651; A61N 2005/0662; A61N 2005/0663; A61N 5/0603; A61N 5/0616; A61N 5/0624; A61N 5/067; A61N 1/00; A61N 5/00; A61N 5/01; A61N 1/40; A61N 2007/0004; A61N 1/10; A61B 18/203; A61B 2018/00452

See application file for complete search history.

(56) References Cited

U.S. PATENT DOCUMENTS

| | | | |
|---|---|---|---|
| 5,130,997 A * | 7/1992 | Ortiz | A61B 18/20 372/103 |
| 5,292,362 A | 3/1994 | Bass et al. | |
| 5,391,550 A | 2/1995 | Carniglia et al. | |
| 5,464,436 A | 11/1995 | Smith | |
| 5,616,313 A | 4/1997 | Nlliams et al. | |
| 5,642,997 A | 7/1997 | Gregg | |
| 6,221,068 B1 * | 4/2001 | Fried | A61B 18/20 128/898 |
| 6,878,145 B2 | 4/2005 | Brugger et al. | |
| 7,107,996 B2 | 9/2006 | Ganz et al. | |
| 7,621,745 B2 | 11/2009 | Bornstein | |
| 2003/0158111 A1 | 8/2003 | Bar-Or | |
| 2003/0232303 A1 | 12/2003 | Black | |
| 2004/0009598 A1 | 1/2004 | Hench et al. | |
| 2004/0199227 A1 | 10/2004 | Altshuler et al. | |
| 2004/0259053 A1 | 12/2004 | Bekov et al. | |
| 2006/0087816 A1 | 9/2006 | Rabiei et al. | |
| 2006/0210494 A1 | 9/2006 | Rabiei et al. | |
| 2006/0241595 A1 | 10/2006 | Kurtz | |
| 2007/0021807 A1 | 1/2007 | Kurtz | |
| 2008/0033514 A1 | 2/2008 | Kurtz | |
| 2008/0033515 A1 | 2/2008 | Kurtz | |
| 2008/0060148 A1 | 3/2008 | Pinyayev | |
| 2009/0087816 A1 | 4/2009 | Bornstein | |
| 2010/0029549 A1 | 2/2010 | Chaput et al. | |
| 2010/0076526 A1 | 3/2010 | Krespi et al. | |
| 2010/0098746 A1 | 4/2010 | King | |
| 2012/0251972 A1 | 10/2012 | Kalmeta | |
| 2012/0330288 A1 | 12/2012 | Clementi et al. | |

(56) References Cited

U.S. PATENT DOCUMENTS

| | | |
|---|---|---|
| 2013/0267943 A1 | 10/2013 | Hancock |
| 2014/0074090 A1* | 3/2014 | Lam ............... A61B 18/042 606/49 |
| 2014/0113243 A1 | 4/2014 | Boutoussov et al. |
| 2014/0141389 A1 | 5/2014 | Kalmeta |
| 2015/0164618 A1 | 6/2015 | Heacock et al. |
| 2015/0283287 A1 | 10/2015 | Agarwal et al. |
| 2017/0120070 A1 | 5/2017 | Kalmeta |

FOREIGN PATENT DOCUMENTS

| | | |
|---|---|---|
| WO | 2007/027620 A1 | 3/2007 |
| WO | 2008/068749 A1 | 6/2008 |
| WO | WO 2011/096003 * | 8/2011 |
| WO | 2012130771 | 10/2012 |
| WO | 2017083579 A1 | 5/2017 |

OTHER PUBLICATIONS

Asai et al. "Maxillary Sinus Augmentation Model in Rabbits" Effect of Occluded Nasal Ostium on New Bone Formation. (2002) Clin. Oral Impl. Res. 13:405-409.

Goldstep—www..oralhealthjournal.com—Diode Lasers for Periodontal Treatment: The story so far. Publication Dec. 2009, p. 44-46.

Ozcelik—http://www.ncbi.nlm.nih.gov/pubmed/148081859—Enamel matrix derivative and low-level laser therapy in the treatment of intra-bony defects: a randomized placebo-controlled clinical trial—J. Clin. Periodontol. Feb. 2008. 35(2):56-147. Epub Dec. 13, 2007.

IP Australia, Examination Report issued in AU Patent Application No. 2020200444, dated May 24, 2021, pp. 1-6.

Schwarz et al., "The impact of laser application on periodontal and peri-implant wound healing", Periodontol 2000, Aug. 20, 2009, pp. 79-108, vol. 51.

Amorim et al., "Clinical study of the gingiva healing after gingivectomy and low-level laser therapy", Photomed Laser Surg., 2006, pp. 588-594, vol. 24(5).

Rodrigues et al., "Modulation of phosphate/pyrophosphate metabolism to regenerate the periodontium: a novel in vivo approach", J Periodontol, Dec. 2011, pp. 1757-1766, vol. 82(12).

Koort et al., "A combined device for optimal soft tissue applications in laster dentistry", Laser Industry Report, Jan. 2013, pp. 24-29.

United States Patent and Trademark Office, Non-Final Office Action issued in U.S. Appl. No. 15/811,651, dated Jul. 15, 2021.

European Patent Office, Extended European Search Report issued in EP Patent Application No. 17870468.0, dated Oct. 28, 2020, pp. 1-14.

United States Patent and Trademark Office, Final Office Action issued in U.S. Appl. No. 16/349,222, dated Feb. 18, 2022, p. 9.

United States Patent and Trademark Office, Non-Final Office Action issued in U.S. Appl. No. 15/348,793, dated Nov. 12, 2021, p. 1-9, PTO-892.

* cited by examiner

Fig. 8  4-15-10
Fig. 9  2-22-11

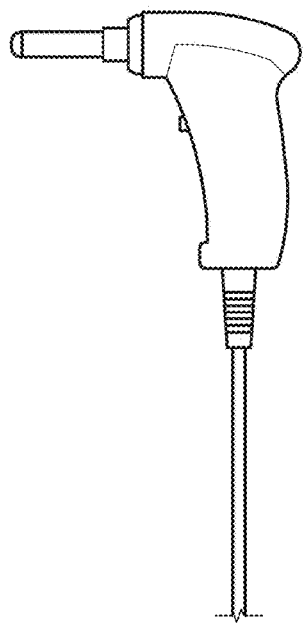
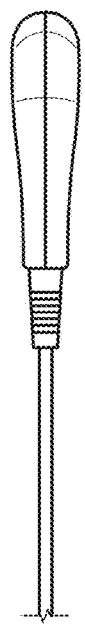
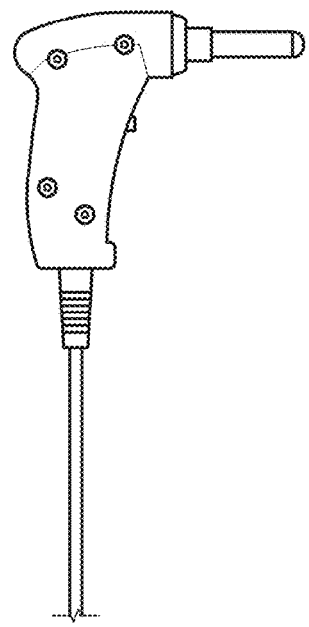
FIG. 17A     FIG. 17B     FIG. 17C
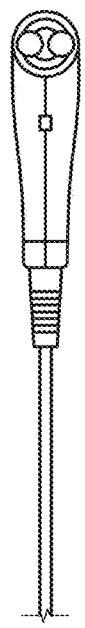
FIG. 17E
FIG. 17F
FIG. 17D

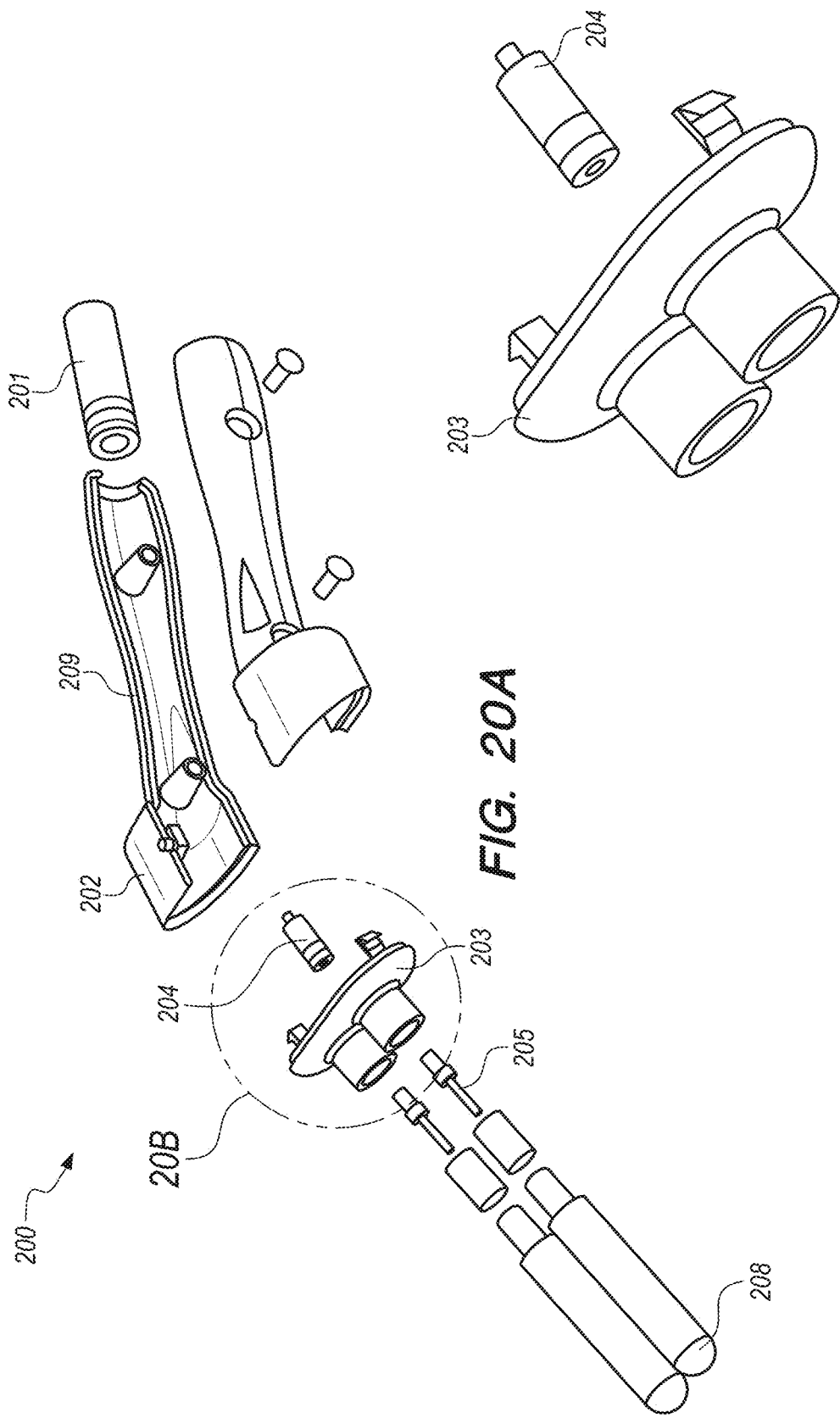

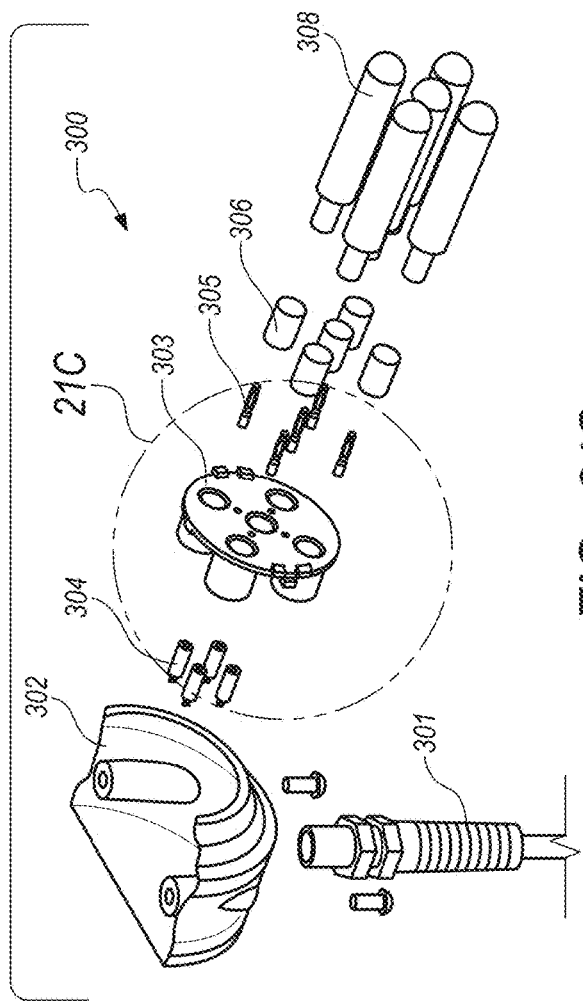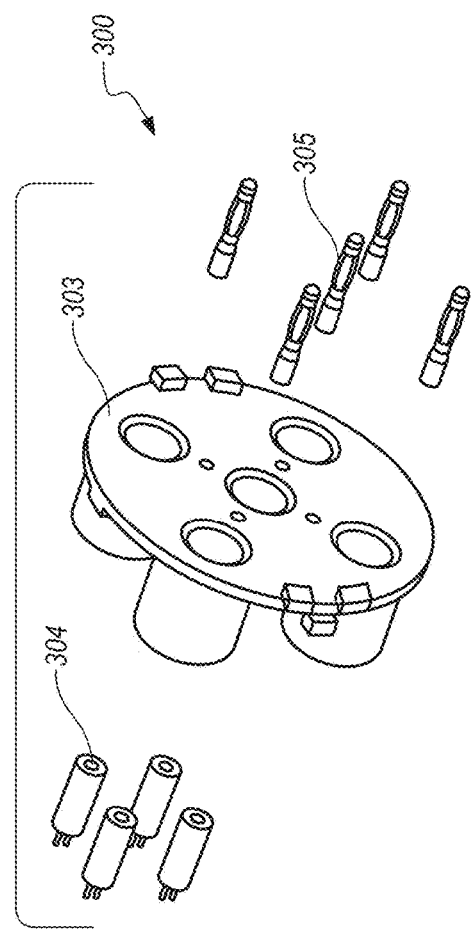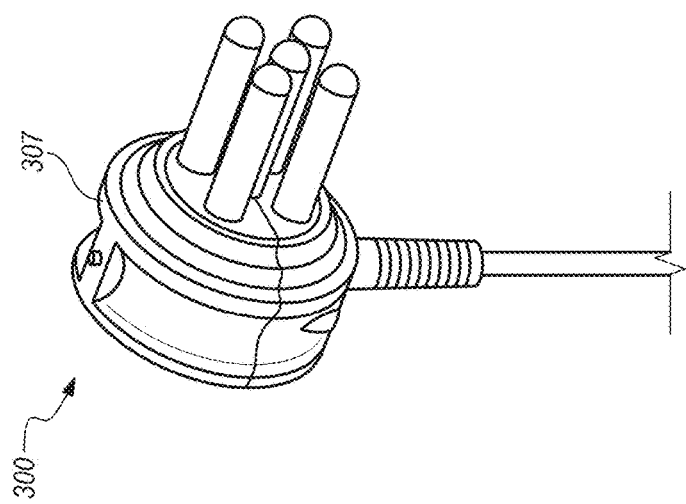

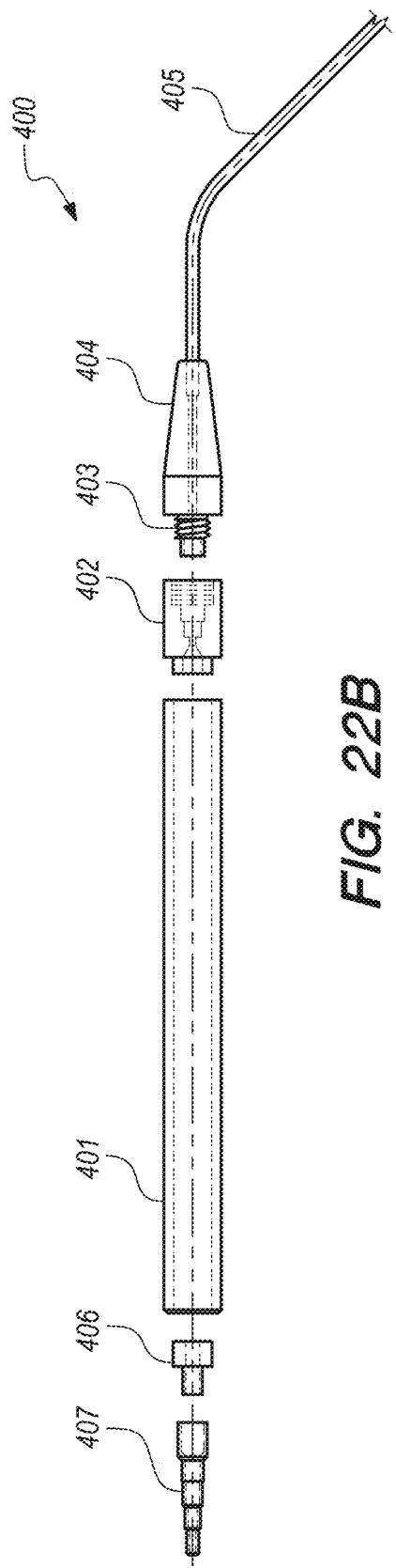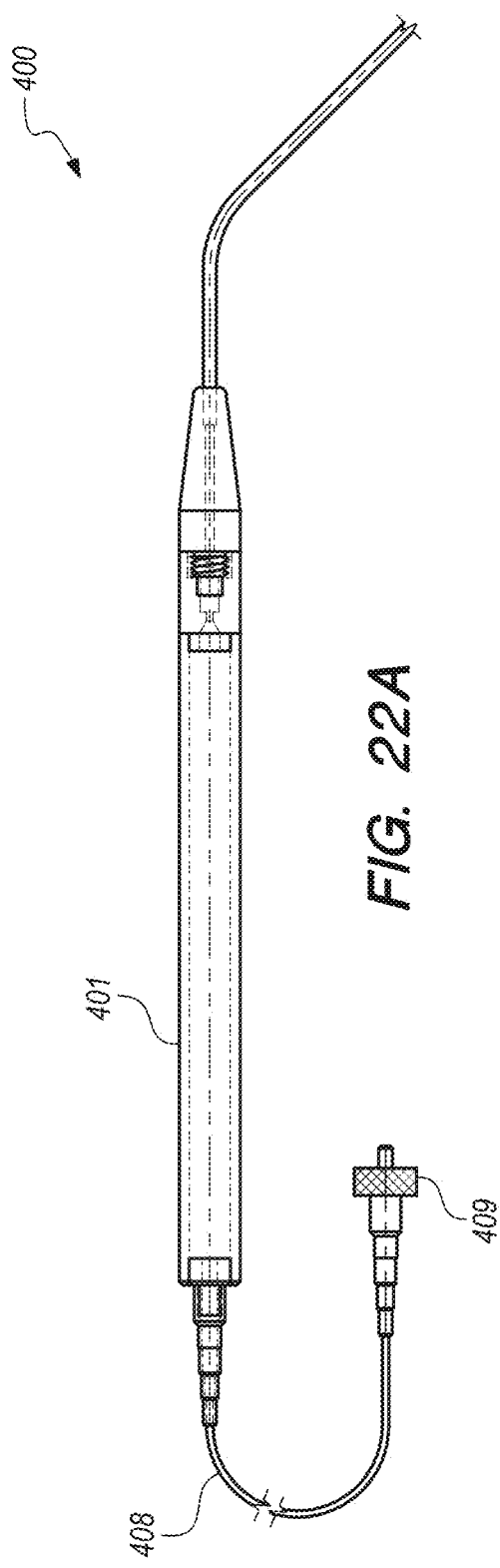
FIG. 22B
FIG. 22A

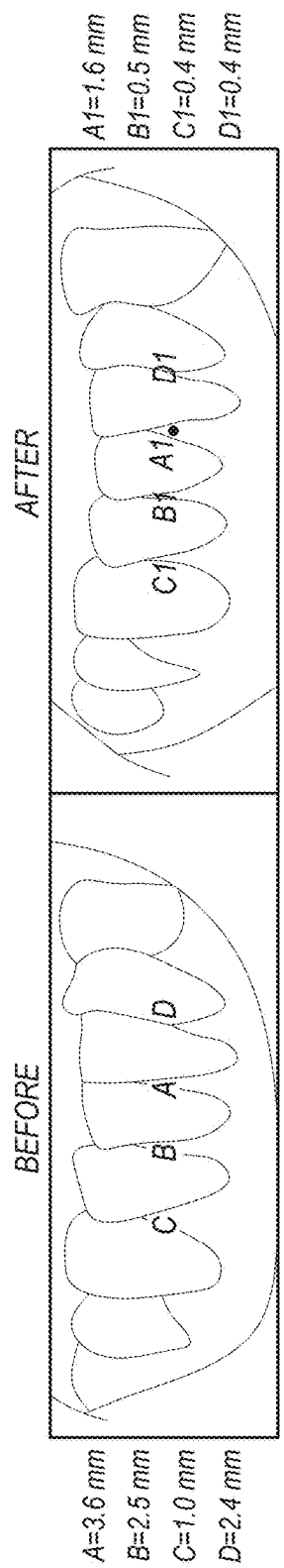
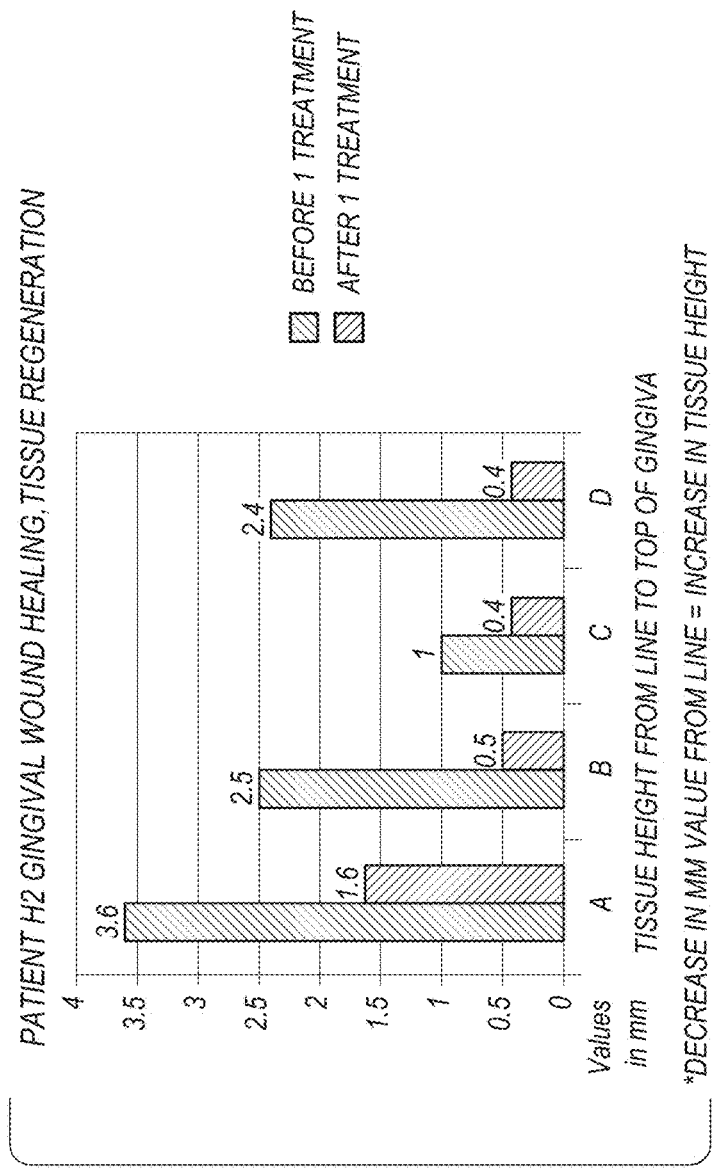

LASER ASSISTED WOUND HEALING PROTOCOL AND SYSTEM

CROSS REFERENCES

This application is a Continuation-In-Part patent application claiming the benefit of priority under 35 U.S.C. 120 from U.S. patent application Ser. No. 13/864,226 filed Apr. 16, 2013, now issued U.S. Pat. No. 9,180,319, which claims the benefit of priority from U.S. patent application Ser. No. 13/078,757 filed Apr. 4, 2011, now abandoned, the entire contents of which are herein incorporated by reference.

FIELD OF THE INVENTION

The present invention relates generally to a method of treating gum diseases using a soft tissue diode laser which produces a beam of light having a wavelength in the visible portion of the electromagnetic spectrum (400 nm-700 nm). Optionally, the laser light utilizes green wavelength range (520-570 nm) at a laser power 0.001 W to 5 W to treat wounds of the soft tissue.

BACKGROUND OF THE INVENTION

Laser Assisted Periodontium and Osseous Regeneration (LAPOR) is a protocol which is laser assisted with the use of a substrate such as but not limited the LAPOR periodontal solution, the LAPOR periodontal gel and the LAPOR substrate and thus causes an increase in cell attachment of epithelial cells, gingival fibroblasts, PDL fibroblasts and adhesion of osteogenic cells. Enhanced cell migration and proliferation appears to lead to accelerated wound fill rates in vitro using PDL fibroblasts, gingival fibroblasts and osteoblast-like cells.

A substrate such as the LAPOR periodontal solution, the LAPOR periodontal gel and the LAPOR substrate, used in the LAPOR protocol, stimulates total protein synthesis and the synthesis of specific extracellular matrix molecules. Studies that evaluate the bone remodeling regulation system indicate that proteins influence this regulation system, thus indicating an indirect involvement in the bone remodeling process. When used in conjunction with three specially formulated periodontal and wound healing substrates, and LAPOR gel root conditioner, LAPOR has shown to stimulate total tissue and bone synthesis, increase gingival attachment, gingival height, bone density, bone height thereby showing accelerated wound fill rates in vivo.

The soft tissue diode laser used produces a beam of light having a wavelength in the visible portion of the electromagnetic spectrum (400 nm-700 nm). Optionally, a beam of light having a wavelength in the green wavelength range (520-570 nm) at a laser power of 0.5 to 1.2 W is used in the LAPOR protocol. It has been shown by the LAPOR protocol to biostimulate the healing and regenerative processes of the periodontium, including the biostimulation of new bone and its supporting elements. The soft tissue diode laser used in the LAPOR protocol, biostimulates the healing response of the periodontium nonsurgically, and biostimulates the tissue regeneration of the periodontium, nonsurgically, and prevents long junctional epithelium from migrating downwards into the sulcus (a biomechanical aspect of tissue healing), thereby preserving the tissue height. A soft tissue diode laser used in the LAPOR protocol helps a substrate such as but not limited to proteins to stimulate total protein synthesis and the synthesis of extracellular matrix molecules, nonsurgically.

Alternatively, the LAPOR protocol may use a beam of light having a wavelength in the green wavelength range (520-570 nm), red wavelength range (620-750 nm), or yellow wavelength range (570-590 nm) having an alternative wattage of 0.001 W to 5 W, preferably 0.002 W to 4 W, more preferably 0.003 W to 4 W, and most preferably 0.005 W to 2 W. The soft tissue diode laser used helps the substrates stimulate total tissue and bone synthesis by biostimulating the healing response and bone/tissue regeneration and its supporting elements of the wound.

SUMMARY OF THE INVENTION

In an exemplary embodiment of the present invention, there is disclosed a method of treating wounds, including gum disease and gingival tissues post scaling/root planning, using a soft tissue diode laser which generates a beam of light having a wavelength in the visible portion of the electromagnetic spectrum (400 nm-700 nm). Optionally, a beam of light having a wavelength in the green range (520-570 nm) at a laser power of 0.5 to 1.2 watts is used to decontaminate the gum tissue and to biostimulate healing and regenerate the periodontium (including cementum of the root surface), thus preventing long junctional epithelium from migrating downwards into the sulcus and thereby preserving the tissue height. Alternatively, a beam of light having a wavelength in the green wavelength range (520-570 nm), red wavelength range (620-750 nm), or yellow wavelength range (570-590 nm) having an alternative wattage of 0.001 W to 5 W may be used to biostimulate healing and regenerate the wound site, its tissue and bone. In a preferred embodiment, the wattage is in the range of 0.002 W to 4 W, more preferred in the range of 0.003 to 3 W, and most preferred in the range of 0.005 W to 2 W. The soft tissue diode laser also biostimulates the healing and regenerative response induced by a substrate, i.e. the LAPOR periodontal and wound healing solution, the LAPOR periodontal gel and the LAPOR periodontal and wound healing substrates, the method comprising: 1) placing the laser inside the sulcus; 2) penetrating the entire sulcus by moving the laser light intermittently vertically and horizontally throughout the sulcus; and 3) placing the substrate in the sulcus prior to a blood clot forming (which then increases cell attachment, adhesion, migration and proliferation).

In an alternative embodiment, the LAPOR protocol may use a radiofrequency (RF) wave to decontaminate the gum tissue and biostimulate healing and regenerate the periodontium. The RF beam is used at 10 W or lower on wounds to assist in new cell organization and hence tissue regeneration. A carrier wave (sine wave) transports a non-sinusoidal waveform to the treatment location. The carrier wave frequency may be in the range of 0.1 MHz to 20 MHz while the non-sinusoidal waveform may be in the range of 0 to 40 KHz. In a preferred embodiment, the carrier wave frequency is in the range of 0.2 MHz to 10 MHz, preferably 0.3 MHz to 5 MHz. Optionally the 0.001 W to 10 watt range, preferably a 0.001 W to 3 W range, is utilized in the hertz range of 40 Hz to 24 GHz. In a further alternative embodiment, the RF wave is a single sine wave. In a further alternative embodiment, the RF wave is more than one sine wave wherein the more than one demonstrates a harmonics pattern.

In another embodiment of the present invention, there is disclosed a root/bone/cartilage conditioner comprised of EDTA 15%, calcium gluconate 20%, methylparaben, propylparaben, Ethanolamine as a buffering agent, carboxymethylcellulose, and green food coloring and sterile water.

In still another embodiment of the present invention, there is disclosed a first substrate comprised of: a combination of mono or disodium phosphate and sodium hydroxide in solution with a sodium content of 11 mg/100 g; 60% water; 9% Lysine; 9% Proline; 9% all other essential amino acids wherein the amino acids are chosen from the group consisting of Isoleucine, Leucine, Methionine, Phenylalanine, Threonine, Tryptophan, Valine, Histadine, Asparagine and Selenocysteine; 2% of all other non-essential amino acids wherein the amino acids are chosen from the group consisting of Alanine, Arginine, Aspartate, Cysteine, Glutamate, Glutamine, Glycine, Serine, Tyrosine and Pyrrolsine; 6.9% free bases wherein the free bases are chosen from the group consisting of adenosine, uridine, guanosine, iridin and cytidine; 2% phosphates wherein the phosphates are chosen from the group consisting of ADP, ATP and acetycholine; and 1% benzoic acid.

In still another embodiment of the present invention, there is disclosed a second substrate comprised of: tricalcium phosphate wherein the tricalcium phosphate is precipitated with calcium hydroxide/Claw oil; and hydroxyapatite crystals.

In yet another embodiment of the present invention, there is disclosed a third substrate comprised of: 5.1% hyaluronic acid; 8% fatty acids wherein the fatty acids are chosen from the group consisting of Linoleic acid (LA), alpha-linolenic acid (ALA), 4.4% sugars wherein the sugars are chosen from the group consisting of mannose, galactose, N-acetylglactosamine, N-acetylglucosamine, N-acetylneuraminic acid, fucose (L configuration minus a carboxyl group at the 6 position), and xylose; 2.2% mixture of glucose and fucose (L configuration minus a carboxyl group at the 6 position); 3% lipids wherein the lipids are chosen from the group consisting of vitamin A, vitamin D2, D3, vitamin E, vitamin K1, K2, vitamin B12 (methylcobalamin, hydroxocobalamin), cholesterol, and diaglycerol; 2.7% vitamins wherein the vitamins are chosen from the group consisting of vitamin B1, vitamin B2, vitamin B3, vitamin B5, vitamin B6, vitamin B7, vitamin B9, vitamin C and pantothenic acid; 4.5% electrolyte sources: wherein the electrolyte sources are chosen from the group consisting of Calcium Chloride, Choline Chloride, Magnesium Sulfate, Potassium Chloride, Potassium Phosphate (monobasic), Sodium Bicarbonate, Sodium Chloride, and Sodium Iodide; 6% metals wherein the metals are chosen from the group consisting of Ag nanoparticles and Au nanoparticles; 3.9% ionic metals wherein the ionic metals are chosen from the group consisting of copper, zinc, selenium, iron, manganese, cobalt, chromium, boron, and molybdenum; and 4% other ionic metals wherein the other ionic metals are chosen from the group consisting of boron, silicon, nickel and vanadium.

In another embodiment of the present invention, there is disclosed as fourth substrate comprised of a tricalcium phosphate and/or collagen limed and/or collagen unlimed.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

FIG. 8 shows an X-Ray view of the upper teeth before treatment with a soft tissue diode laser after treatment with a substrate.

FIG. 9 shows an X-ray view of the upper teeth of FIG. 8 after treatment with a soft tissue diode laser after treatment with a substrate.

FIG. 17a-17f show various views of a first embodiment of a diode laser of the present invention. (a) shows a right side view. (b) shows a back side view. (c) shows a left side view. (d) shows a front side view. (e) shows a top view. (f) shows a bottom view.

FIGS. 20a and 20b an exploded view of the diode laser of FIG. 19. (a) shows an exploded view. (b) shows a close-up of the laser housing.

FIG. 21a-21c show various view of a third embodiment of the diode laser of the present invention. (a) shows a side perspective view. (b) shows an exploded view. (c) shows a close up view of the laser housing.

FIG. 22a-22c shows a fiber optic laser of the present invention. (a) shows an assembled view. (b) shows an exploded view. (c) shows a fully assembled laser.

FIG. 26a-26c show gingival wound healing and tissue regeneration measurements before and after treatment. (a) shows wounds before treatment. (b) shows tissue regeneration after treatment. (c) shows tissue height measurements before and after treatment.

DETAILED DESCRIPTION OF THE INVENTION

Definitions

Figure 1:
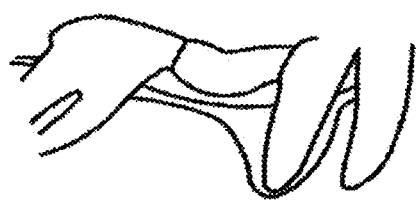
FIG. 1 shows an X-Ray view of a patient's teeth before treatment with a soft tissue diode laser before a substrate has been applied.
Figure 2:
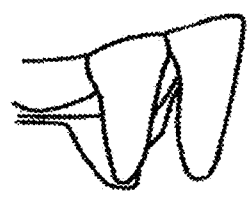
FIG. 2-7 show X-Ray views of the lower teeth of FIG. 1 after treatment with a soft tissue diode laser after treatment with a substrate.
Figure 3:
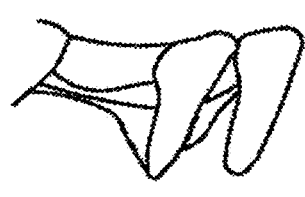
Figure 4:
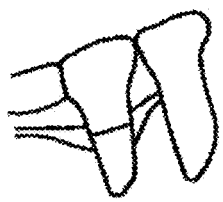
Figure 5:
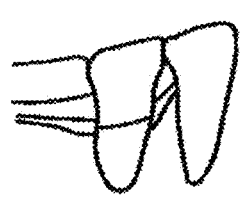
Figure 6:
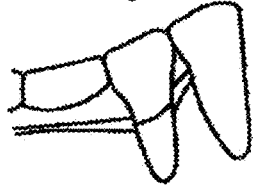
Figure 7:

As used herein, the term "gum disease" means periodontal disease which can lead to tooth loss and/or other health problems. Examples of periodontal disease include gingivitis, aggressive periodontitis, chronic periodontitis, periodontitis as a manifestation of systemic diseases, and necrotizing periodontal disease.

As used herein, the term "patient" means any individual suffering from a disease of the gums and in need of treatment for said gum disease.

As used herein, the term "locus" means an exact point of measurement within the sulcus or the immediate surrounding area.

As used herein, the term "substrate mixture" means the mixture of the first substrate and the second substrate disclosed herein for treatment of gum disease.

As used herein, the term "bone regeneration" means increasing the density of calcium at specific loci in or around the sulcus.

As used herein, the term "calcium density" means the measurement of calcium mass around a given loci.

As used herein the term "wound" means any area that has lost any original tissue or bone or any other structure not named that previously existed in a healthy non-wounded, undamaged and unaged form.

The LAPOR protocol can be used in the treatment of gum disease and wounds by combining the most effective methods of treatment with the use of a special laser. Approximately 66% of the United States population has some form of gum disease. But many avoid seeking treatment because of the discomfort that often results from gum surgery. LAPOR provides a new choice. The LAPOR protocol is a treatment that is more effective as traditional periodontal surgery, and it is much more beneficial to the patient both in the short term and in the long run.

The LAPOR protocol takes only about an hour and only two short follow-up visits. Patients enjoy no downtime with recovery taking only 24 hours. This makes immediate return to work both possible and comfortable.

After having the LAPOR protocol performed, gum recession is zero when compared to that which most often follows normal periodontal surgery. This, combined with new cementum formation on the roots, bone formation in previous defects, periodontal ligament formation and no tooth loss.

The LAPOR protocols of the present invention can be used to heal wound sites by combining the most effective methods of treatment with the laser, radiofrequency energy and substrates. Following performance of treatment protocols, no receding of tissue from the wound site was observed. In a preferred embodiment, the RF energy waves may be up to 10 W. The carrier wave frequency may be in the range of 0.1 MHz to 20 MHz while the non-sinusoidal waveform may be in the range of 0 to 40 KHz. In a preferred embodiment, the carrier wave frequency is in the range of 0.2 MHz to 10 MHz, preferably 0.3 MHz to 5 MHz. Optionally a 0.001 W to 10 W range RF energy, preferably a 0.001 W to 3 W range, is utilized in the hertz range of 40 Hz to 24 GHz. In a further alternative embodiment, the RF wave is more than one sine wave wherein the more than one demonstrates a harmonics pattern.

The special type of laser used in the LAPOR protocol is the diode, a semiconductor coherent light beam used on soft tissues. The laser light used has a wavelength in the visible portion of the electromagnetic spectrum, between 400 nm-700 nm wavelength. Optionally, the green range (520-570 nm) of the visible spectrum is utilized at a laser power of 0.5 to 1.2 watts, which disinfects the site, leaving the gum tissue bacteria free, and biostimulates healing; in conjunction with treatment with a substrate, the laser biostimulates regeneration of the periodontium. Traditional periodontal therapy removes tissue height of a tooth to reduce the pocket depths. The LAPOR protocol is a regenerative procedure. The patient does not lose tissue volume. Tissue volume is increased and bone is regenerated.

The use of the diode laser in conjunction with routine scaling and root planning is more effective than scaling and root planning alone. It enhances the speed and extent of the patients gingival healing and postoperative comfort. This is accomplished through laser bacterial reduction and biostimulation with a laser light having a wavelength in the visible portion of the electromagnetic spectrum, between 400 nm-700 nm wavelength. Optionally, the green range (520-570 nm) of the visible spectrum is utilized at a laser power of 0.5 to 1.2 watts. Alternatively, the laser power wattage may be in the range of 0.001 W to 5 W, preferably 0.002 W to 4 W, more preferably 0.003 W to 3 W, and most preferably 0.005 W to 2 W.

Figure 10:
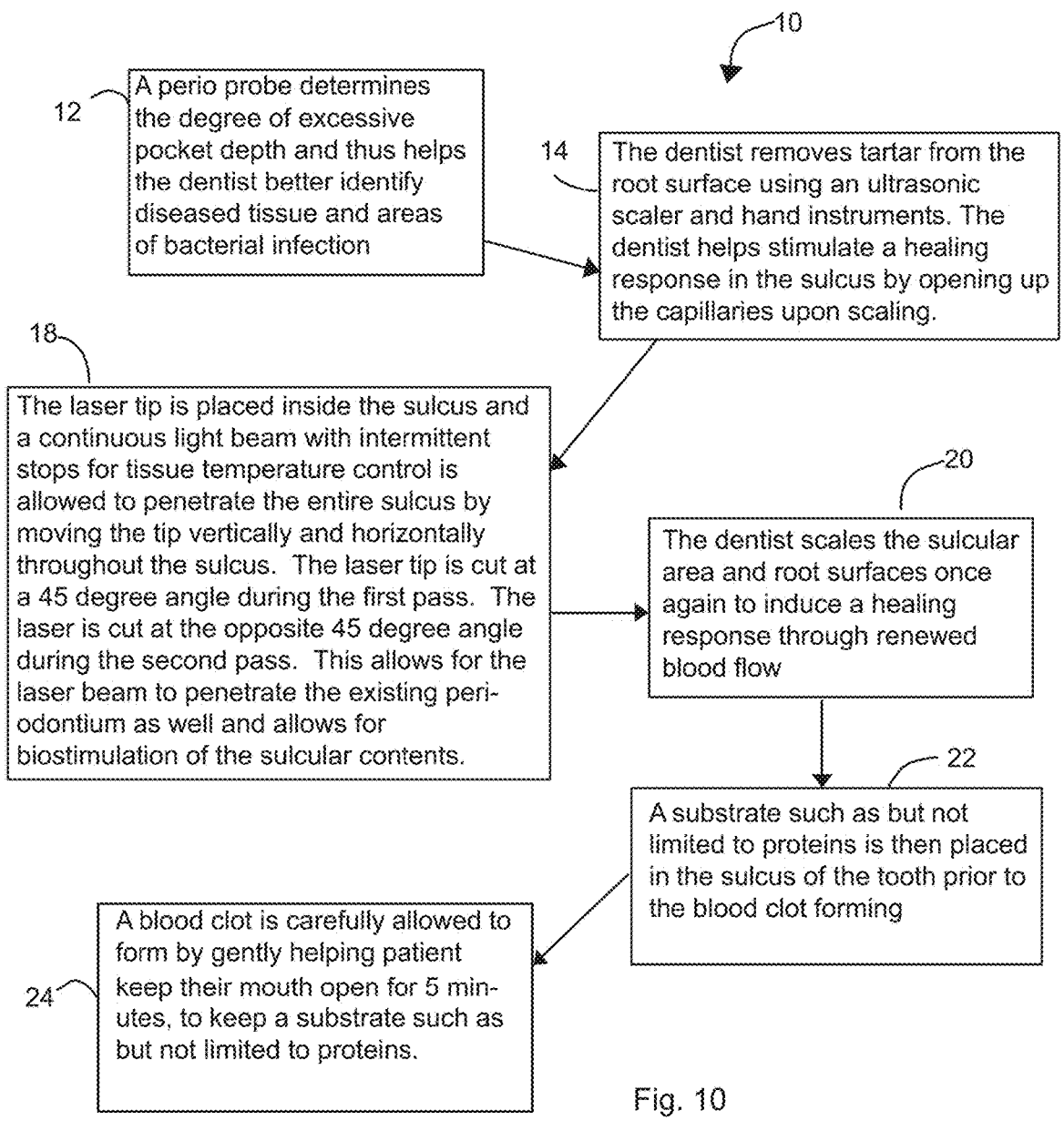
FIG. 10 shows a flow diagram of a method of using a soft tissue diode laser to treat gum disease in accordance with the principles of the invention.

Referring to FIG. 10, there is disclosed a method 10 of using a soft tissue diode laser which produces a beam of light, used intermittently, having a wavelength in the visible portion of the electromagnetic spectrum, between 400 nm-700 nm wavelength. Optionally, the green range (520-570 nm) of the visible spectrum is utilized at a laser power of 0.5 to 1.2 watts to treat gum disease. Starting at block 12, a perio probe determines the degree of excessive pocket depth and thus helps the dentist better identify diseased tissue and areas of bacterial infection. The dentist removes calculus from the root surface using an ultrasonic scaler and hand instruments, block 14. This action by the dentist helps stimulate a healing response in the sulcus by opening up the capillaries upon scaling. Going to block 18, the laser tip is placed inside the sulcus and a continuous light beam with intermittent stops for tissue temperature control is allowed to penetrate the entire sulcus by moving the tip vertically and horizontally throughout the sulcus. The laser tip is cut at a 45 degree angle during the first pass. The laser is cut at the opposite 45 degree angle during the second pass. This allows for the laser beam to penetrate the existing periodontium to decontaminate the tissue, as the heat of the targeted laser light kills the bacteria. This also allows for biostimulation of the sulcular contents. At block 20, the dentist scales the sulcular area and root surfaces once again to induce a healing response through renewed blood flow. Going to block 22, at least one substrate, such as but not limited to matrix proteins, is then placed in the sulcus of the tooth prior to the blood clot forming and at block 24, a blood clot is carefully allowed to form by gently helping patient keep their mouth open for 5 minutes, to keep the substrate intact.

Alternatively, the laser tip is a specially designed tip that disperses light energy throughout the wounded sulcus which allows the laser beam to penetrate the existing tissues to decontaminate the tissue, as the heat of the targeted laser light kills the bacteria and as a result block 20 may be eliminated going directly to block 22

The LAPOR protocol is much less invasive than traditional surgery and offers advantages and benefits over its counterpart. Recovery time is much faster because most, if not all, damage to healthy tissue is avoided through the use of more advanced technology. Because the LAPOR protocol leaves healthy tissue intact, the height of the gums themselves increases around the teeth and is better preserved. The LAPOR protocol prevents long junctional epithelium from migrating downwards into the sulcus, thus preserving the tissue height and allowing for the regeneration of the periodontium.

Figure 18A:
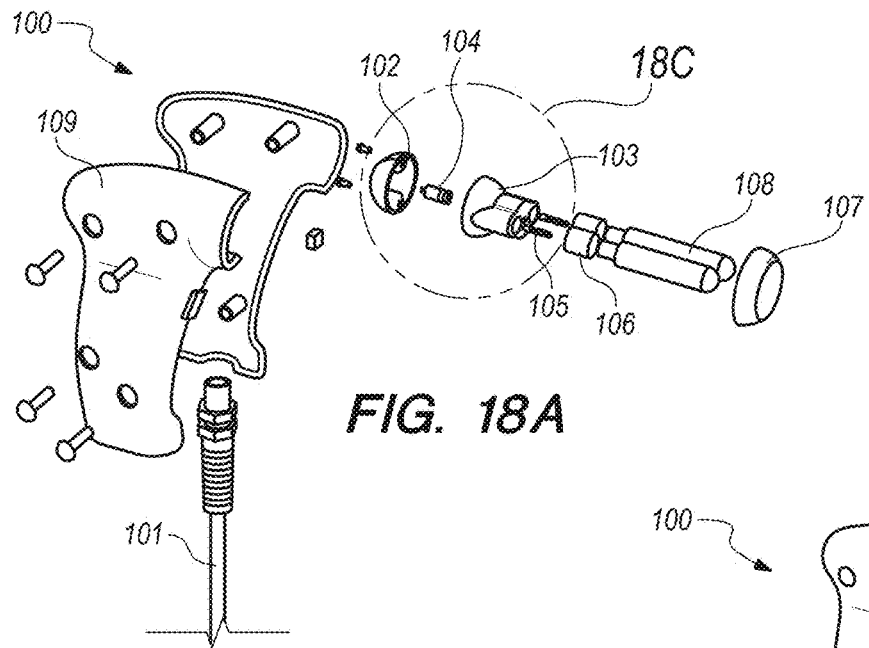
FIG. 18a-18c show an exploded view of the diode laser of FIG. 17. (a) shows an exploded view. (b) shows an assembled view. (c) shows a close-up of the laser housing.
Figure 18B:
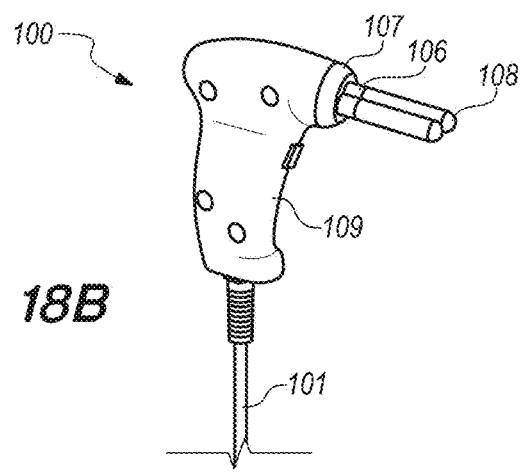
Figure 18C:
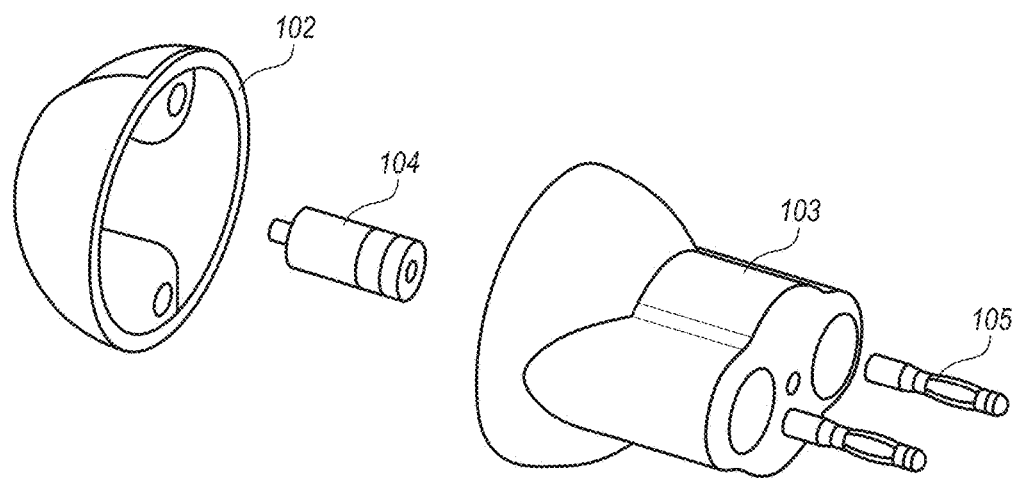
Figure 19A:
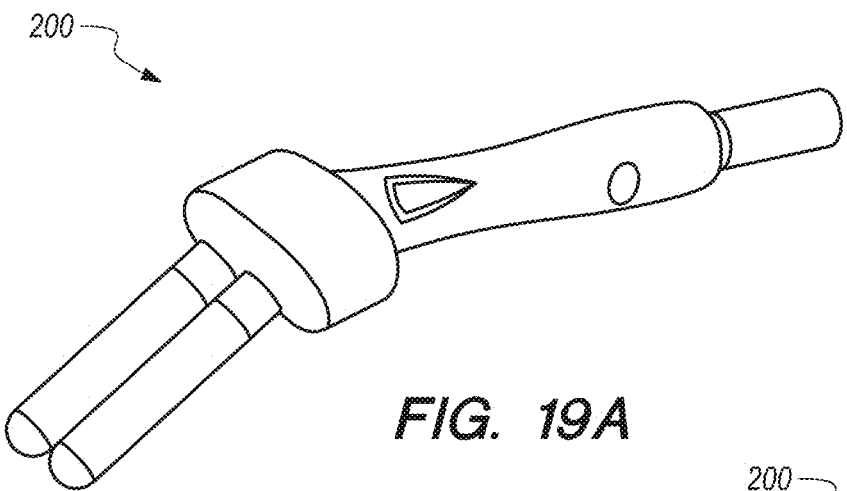
FIG. 19a-19g shows various views of a second embodiment of a diode laser of the present invention. (a) shows a top perspective view. (b) shows a back view. (c) shows a left side view. (d) shows a top view. (e) shows a front perspective view. (f) shows a right side view. (g) shows a bottom view.
Figure 19B:
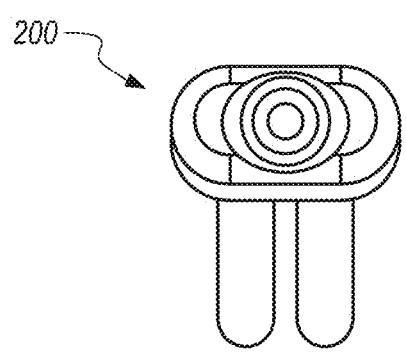
Figure 19C:
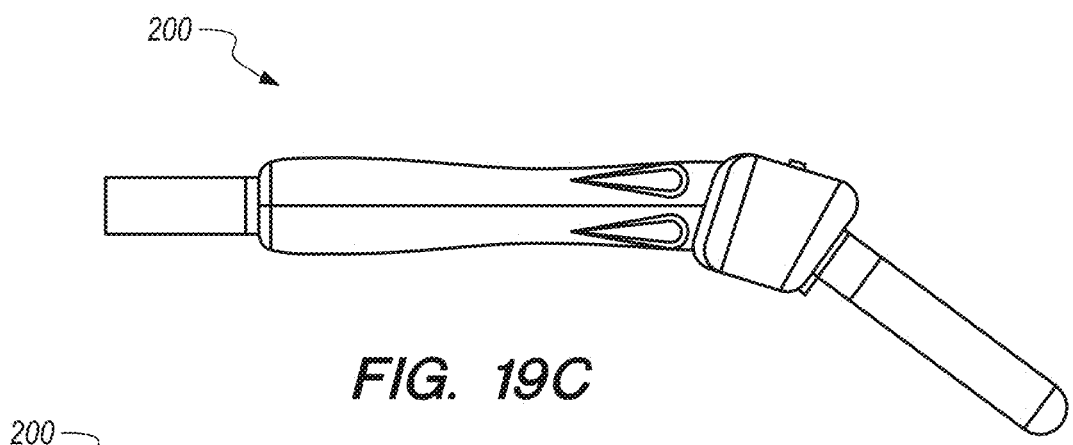
Figure 19D:
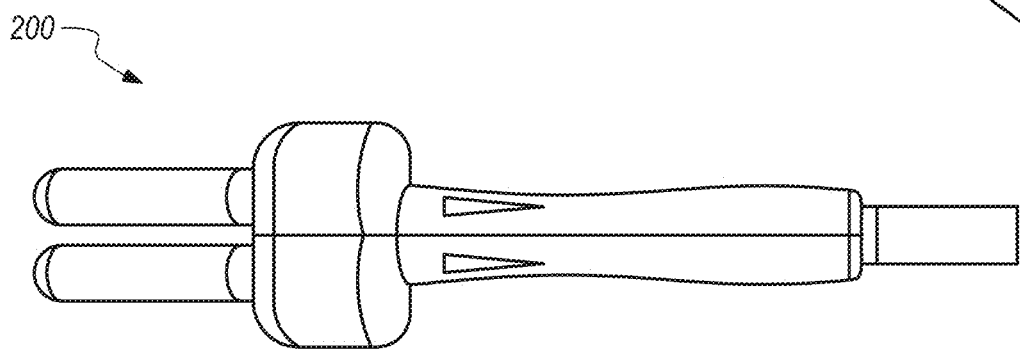
Figure 19E:
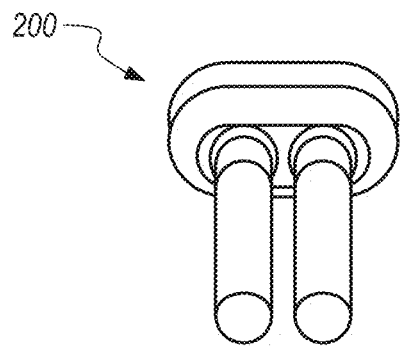
Figure 19F:
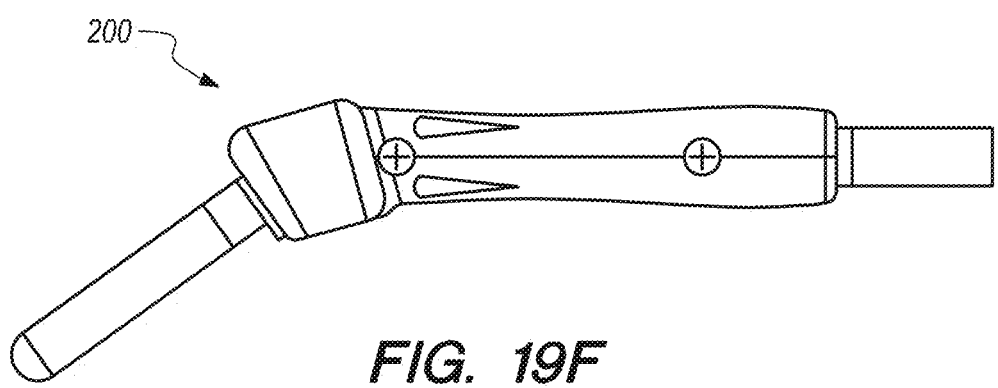
Figure 19G:
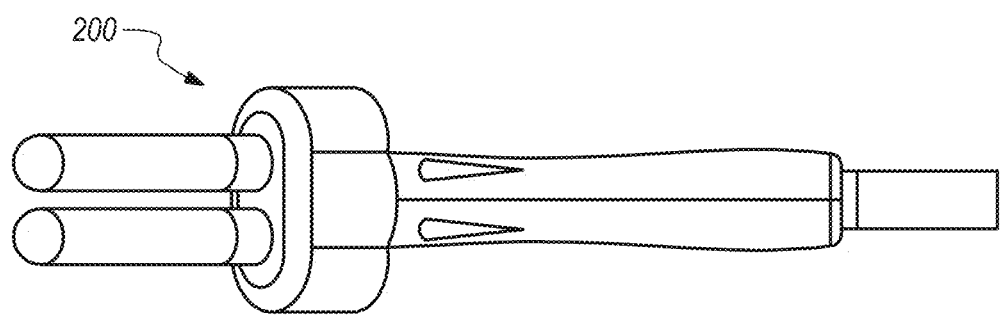

Referring to FIG. 17a-17f, shown are various angles of the first embodiment of a device 100 for use in conjunction with the substrates and methods of the present invention. FIGS. 18a and 18b show perspective views of the device 100 in the first embodiment. Specifically, FIG. 18a illustrates an exploded view of the device 100 comprised of cord 101 integrally connected to handle 109, handle 109 further connected to heat sink 102. Housing 103 securely connects to heat sink 102 thereby creating a cavity between the housing 103 and heat sink 102. Laser 104 is positioned within the cavity between housing 103 and heat sink 102. Male connectors 105 connect RF source 108 to housing 103 wherein threaded inserts 106 cover the connection therebetween. Cap 107 is positioned over housing 103 and secures to handle 109. FIG. 18c shows a detailed view of heat sink 102, laser 104, housing 103 and male connectors 105 in relation to each other. In a preferred embodiment, the device 100 may have a plurality of RF sources 108 wherein a plurality is defined as at least two tips (i.e. dipole). Housing 103 is capable of movement such that RF source 108 may be adjusted 45° up or down relative to the x-axis for ease of use depending upon the location of the wound receiving treatment.

The laser energy may have wavelength in the green wavelength range (520-570 nm), red wavelength range (620-750 nm), or yellow wavelength range (570-590 nm) having a wattage of 0.001 W to 5 W. In a preferred embodiment, laser energy has a wattage of 0.001 W to 5 W. The wattage is in the range of 0.001 W to 4 W, more preferred in the range of 0.003 to 3 W, and most preferred in the range of 0.005 W to 2 W. The RF energy may have a power of 10 watts or lower. The carrier wave frequency may be in the range of 0.1 MHz to 20 MHz while the non-sinusoidal waveform may be in the range of 0 to 40 KHz. In a preferred embodiment, the carrier wave frequency is in the range of 0.2 MHz to 10 MHz, preferably 0.3 MHz to 5 MHz. Optionally a 0.001 W to 10 W range RF energy, preferably a 0.001 W to 3 W range, is utilized in the hertz range of 40 Hz to 24 GHz. In a further alternative embodiment, the RF wave is more than one sine wave wherein the more than one demonstrates a harmonics pattern.

Referring to FIG. 19a-19g, shown are various angles of a second embodiment of a device 200 for use in conjunction with the substrates and methods of the present invention. FIG. 20a shows a perspective view of the device 200 of the second embodiment. Specifically, FIG. 20a illustrates an exploded view of the device 200 comprised of wire grommet 201 integrally connected to handle 209, handle 209 further comprised of heat sink 202. Housing 203 securely connects to heat sink 202 thereby creating a cavity between the housing 203 and heat sink 202. Laser 204 is positioned within the cavity between housing 203 and heat sink 202. Male connectors 205 connect RF source 208 to housing 203 wherein threaded inserts 206 cover the connection there between. FIG. 20b shows a detailed view of laser 204 and housing 203 in relation to each other.

Referring to FIG. 21a-21c, shown is a third embodiment of a device 300 for use in conjunction with the substrates and methods of the present invention. FIG. 21a shows a perspective view of the device 300 of the second embodiment. Specifically, FIG. 21b illustrates an exploded view of the device 300 comprised of wire grommet 301 integrally connected to housing 303, housing 303 further comprised of heat sink 302. Housing 303 securely connects to heat sink 302 thereby creating a cavity between the housing 303 and heat sink 302. Laser 304 is positioned within the cavity between housing 303 and heat sink 302. Male connectors 305 connect RF source 308 to housing 303 wherein threaded inserts 306 cover the connection there between. FIG. 21c shows a detailed view of laser 304 and housing 303 in relation to each other. By way of example only, the device may have five or six tips.

Figure 22C:
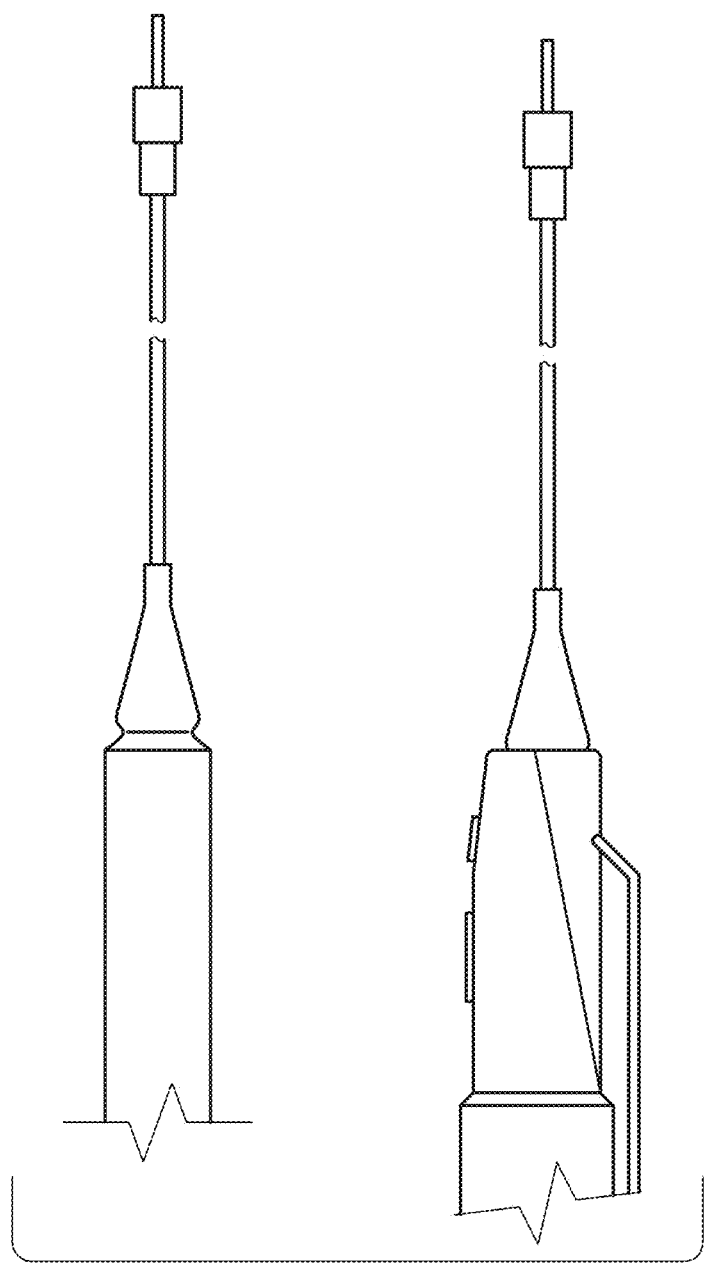
Figure 23:
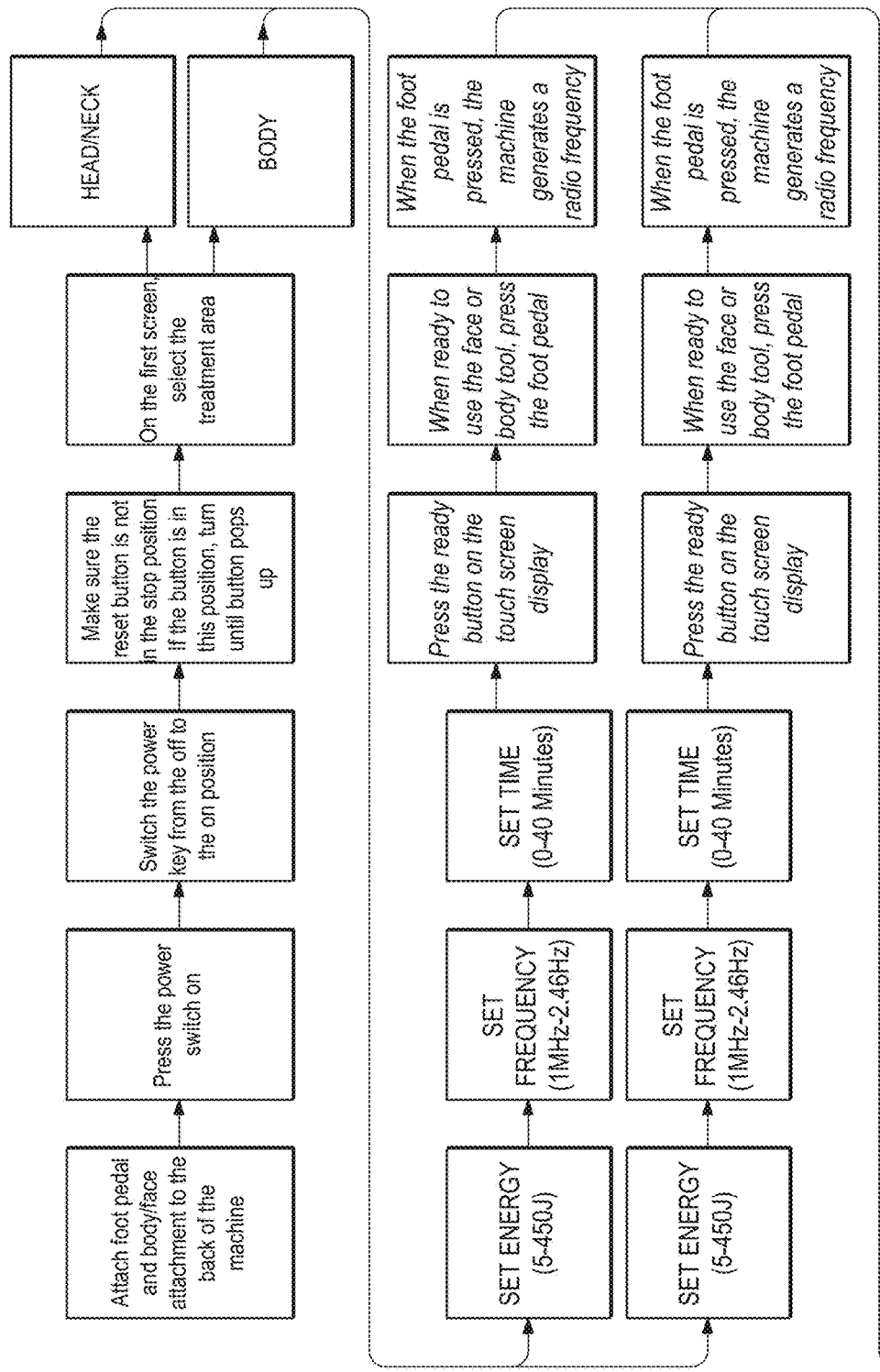
FIG. 23 shows a flow chart of the protocol for using a laser of the present invention.

Referring to FIGS. 22a and 22b, shown is a fiber optic device 400 for use in conjunction with the substrates and methods of the present invention. Fiber optic device 400 is comprised of hand grip assembly 401 disposed between a first end and a second end. The first end is further comprised of nose insert 402 positioned between hand grip assembly 401 and removable nose assembly 404. Bent fiber tube 405 extends from removable nose assembly 405. The second end is further comprised of base insert 406 positioned between hand grip assembly 401 and rubber boot 407. Extending from rubber boot 407 is sheathed fiber 408 having a SMA connector 409 at the end opposite rubber boot 407. FIG. 22c shows a fully assembled fiber optic device 400 further comprising a body for housing the laser source.

Firstly, the root conditioner is applied to the sulcus. The root conditioner comprises the following at Table 1:

TABLE 1

| Component | |
|---|---|
| EDTA | 20-25 g. |
| Calcium gluconate | 10-20 g. |
| Methylparaben | .1-.9 g. |
| Propylparaben | .01-.1 g. |
| Ethanolamine | 2-8 mls. |
| Carboxymethylcellulose | 2-10 g. |
| Green food coloring | 1-2 drops |
| Sterile water | 100 mls. |

The conditioner is optionally rinsed out prior to application of additional substrates or laser light. Alternatively, the conditioner is left in the sulcus, with the laser light being applied prior to application of any substrate. In an alternative embodiment, the conditioner is left in with only one substrate applied prior to application of the laser light. Optionally, the conditioner is left in the sulcus and substrate is added prior to any application of laser light.

The placement of the substrate into the sulcus containing luminesced blood enables the luminesced blood to coagulate upon the substrate.

Optionally, the liquid substrate is comprised of the following, per 1 L of solution, at Table 2:

TABLE 2

| | % |
|---|---|
| Essential Amino Acids | |
| Isoleucine | 1.125 |
| Leucine | 1.125 |
| Methionine | 1.125 |
| Phenylalanine | 1.125 |
| Threonine | 1.125 |
| Tryptophan | 1.125 |
| Valine | 1.125 |
| Histidine | 1.125 |
| Lysine | 9 |
| Non-Essential Amino Acids | |
| Alanine | 0.25 |
| Arginine | 0.25 |
| Aspartate | 0.75 |
| Glutamate | 0.25 |
| Glycine | 0.25 |
| Serine | 0.25 |
| Proline | 9 |
| Phosphates | |
| ADP | 0.667 |
| ATP | 0.667 |
| Acetylcholine | 0.667 |
| Free Bases | |
| Adenosine | 1.725 |
| Uridine | 1.725 |
| Guanosine | 1.725 |
| Cytidine | 1.725 |
| Benzoic Acid | 1 |
| Sodium Chloride | 1.1 |
| Sterile water | 60 |
| Total: | 100 |

Optionally, the total sterile water component is adjusted 20% up or down, depending on the desired viscosity to be achieved.

In an alternative embodiment, the liquid substrate is comprised of the following, at Table 3:

TABLE 3

| | Grams |
|---|---|
| Essential Amino Acids | |
| Isoleucine | 11.25 |
| Leucine | 11.25 |
| Methionine | 11.25 |
| Phenylalanine | 11.25 |
| Threonine | 11.25 |
| Tryptophan | 11.25 |
| Valine | 11.25 |
| Histidine | 11.25 |
| Lysine | 90 |
| Non-Essential Amino Acids | |
| Alanine | 2.5 |
| Arginine | 2.5 |
| Aspartate | 7.5 |
| Glutamate | 2.5 |
| Glycine | 2.5 |
| Serine | 2.5 |
| Proline | 90 |
| Phosphates | |
| ADP | 7-8 |
| ATP | 7-8 |
| Acetylcholine | 6-7 |
| Free Bases | |
| Adenosine | 13-14 |
| Uridine | 13-14 |
| Guanosine | 13-14 |
| Cytidine | 13-14 |
| Iridine | 13-14 |
| Benzoic Acid | 20 |
| Sodium Chloride | .1-.9 |
| Sterile water | .9-1.2 L |

In an alternative embodiment, an additional substrate may be applied, the additional substrate, substrate 3, is comprised of the following at Table 4:

TABLE 4

| | |
|---|---|
| Hyaluronic acid | 200 mg to 5.1 g |

| | Grams |
|---|---|
| Fatty acids | |
| Linoleic acid (LA) | 4 |
| Alpha-linolenic acid (ALA) | 4 |
| | 8 |
| Sugars (except glucose and fucos) | |
| Mannose | 0.6 |
| Galactose | 0.6 |
| N-acetylgalactosamine | 0.6 |
| N-acetylglucosamine | 0.6 |
| N-acetylneuraminic acid | 0.6 |
| Fucose (L config. and no carboxyl at 6 position) | 0.6 |
| Xylose | 0.6 |
| | 4.2 |
| Glucose | 1.1 |
| Fucose (L config. and no carboxyl at 6 position) | 1.1 |
| Lipids | |
| A | 0.3 |
| D2 | 0.3 |
| D3 | 0.3 |
| E | 0.3 |
| K1 | 0.3 |
| K2 | 0.3 |
| B12 (Methylcobalamin) | 0.3 |
| B12 (Nydroxocobalamin) | 0.3 |
| Cholesterol | 0.3 |
| Diaglycerol | 0.3 |
| | 3.0 |
| Vitamins | |
| B1 | 0.3 |
| B2 | 0.3 |
| B3 | 0.3 |
| B5 | 0.3 |
| B6 | 0.3 |
| B7 | 0.3 |
| B9 | 0.3 |
| C | 0.3 |
| Pantothenic acid | 0.3 |
| | 2.7 |
| Electrolyte Sources | |
| Calcium chloride | .5 |
| Choline Chloride | .5 |
| Magnesium Sulfate | .5 |
| Potassium Chloride | .5 |
| Potassium Phosphate-monobasic | 1 |
| Sodium Bicarbonate | .5 |
| Sodium Chloride | .5 |
| Sodium Iodide | .5 |
| | 4.5 |
| Metals | |
| Ag nanoparticles | 0.3 |
| Au nanoparticles | 0.3 |
| | 0.6 |
| Iconic metals | |
| Copper | 0.3 |
| Zinc | 0.3 |

TABLE 4-continued

| | |
|---|---|
| Selenium | 0.3 |
| Iron | 0.3 |
| Manganese | 0.3 |
| Cobalt | 0.3 |
| Chromium | 0.3 |
| Boron | 0.3 |
| Molybdenum | 0.3 |
| | 2.7 |
| Other ionic metals | |
| Boron | 0.3 |
| Silicon | 0.3 |
| Nickel | 0.3 |
| Vanadium | 0.3 |
| | 1.2 |
| Benzoic Acid | Up to 10.1 |
| Sodium Chloride | .1-.9 |
| Sterile water | 60-300 ml |

Optionally, the total sterile water component is adjusted 20% up or down, depending on the desired viscosity to be achieved.

Substrates 1, 2 and 3 may have different modalities of delivery, for example, drops, sprays, injections or intravenous having the same ingredients, as well as sublingual, anal, foam and ointment formulations.

In an alternative embodiment, an additional substrate may be applied, the additional substrate 4 is comprised of the following:

1. collagen, limed or
2. collagen, unlimed, or
3. collagen, supplemented with porous tricalcium phosphate crystals with one size or variety of sizes: 10-50 µm, 50-150 µm, 100-300 µm, 500-1000 µm, 1-3 mm and 3-6 mm. The tricalcium phosphate crystals may be dense or porous.

An additional substrate may be applied, the additional substrate comprised of the following: a mixture of tricalcium phosphate and hydroxyapatite crystals. The tricalcium phosphate is precipitated with CaOH/devil's claw oil, in a preferred embodiment. Optionally, the additional substrate includes 50% tricalcium phosphate/devil's claw oil precipitated with 50% porous hydroxyapatite crystals. The tricalcium phosphate crystals used are granules in the following sizes: 10-50 µm, 50-150 µm, 100-300 µm, 500-1000 µm, 1-3 mm and 3-6 mm. The tricalcium phosphate crystals may be dense or porous.

The additional substrate may be comprised of hydroxyapatite crystals of granules containing the following sizes: 10-50 µm, 50-150 µm, 100-300 µm, 500-1000 µm, 1-3 mm and 3-6 mm. The hydroxyapatite crystals may be dense or porous.

In the following examples, the conditioner is applied and subsequently rinsed out. Optionally, the conditioner is left in the sulcus, as the conditioner allowed the micropores within the tooth structures to remain open.

After the conditioner is applied, the sulcus is biostimulated with a laser light. After this occurs, the liquid substrate is applied. Optionally, the additional substrate is applied. For cavities other than oral cavities, a diluted substrate assists treatment when ingested or taken via IV is beneficial although not required.

The fiber optic device of the present invention is the sole device placed inside the sulcus for treatment. The sulcus may also be treated with laser, RF or laser with RF. The remaining disclosed embodiments of the device may be used in wound treatment in conjunction with the substrates depending on the wound site and severity of the wound.

Substrates disclosed herein may be a form including, but not limited to, liquid, tablet, enema, gel, injection or foam.

Alternative RF and/or Laser Assisted Wounded Tissue Repair:
1. Scale/root plane;
2. Etch root of tooth;
3. Rinse with saline water;
4. Place tip of laser into the sulcular wound and turn the laser on for 5 seconds;
5. Repeat step 4 circumferentially vertically and horizontally around tooth until the entire sulcular wound has been saturated by laser energy;
6. Place Substrate 1 and Substrate 3 into glass dappen dishes;
7. Place collagen (Substrate 4) into glass dappen dish;
8. Place the desired mixture into the sulcular wound where bone/tissue loss occurred;
9. Wait a few seconds;
10. Place more of the mixture into the sulcular wound where bone/tissue damage occurred;
11. Wait a few seconds;
12. Repeat steps 8 until all defects have been filled;
13. Wait 1 minute;
14. Place hand piece with its RF tip, with or without laser, perpendicular to the wound, turn on and keep in position for 1 minute;
15. Wait 10 seconds; and
16. Repeat RF step 14 until entire wound has been covered with RF energy, with or without laser.

Alternative RF and/or Laser Assisted Wounded Tissue Repair:
1. Cleanse wound with saline;
2. Place Substrate 1 and/or 3 onto wound;
3. Direct RF/laser, RF, or laser energy at wound for 1 minute;
4. Place Substrate 3 and/or 4 onto wound;
5. Wait 10 seconds; and
6. Repeat steps 2-5 until wound bed is covered.

Treatment of the oral cavity, head/neck, anal, vaginal region and the deeper areas reached while treating these may be performed with the RF with substrate (applied substrate or drank with water), RF without substrate, RF plus laser with substrate (applied substrate or drank with water), RF plus laser without substrate and laser with substrate (applied substrate or drank with water), laser without substrate. The treatment described may be utilized throughout the gastro-intestinal tract, head/neck and anus. Any energy, applied to the oral cavity and surrounding structures, anal cavity and its surrounding structures, head and neck region and its surrounding structures, may travel to deeper areas. Surrounding structures include, but are not limited to, all bone, cartilage, muscles, tendons, nerves, blood vessels, and epithelium.

RF and/or Laser Assisted Head and Neck Wound Tissue Repair:
1. Drink 4 oz. diluted Substrate 1;
2. Wait 15 minutes;
3. Drink 4 oz. diluted Substrate 3;
4. Wait 15 minutes;
5. Direct RF/laser, RF or laser energy at head and neck location and the surrounding structures where wound occurred;
6. Keep energy in place or move over desired area until desired effect achieved; and
7. Move on to next site until desired result achieved.

Surrounding structures include, but are not limited to, all bone, cartilage, muscles, tendons, nerves, blood vessels, and epithelium.

Head and neck includes, but is not limited to, all structures of the head and neck including esophagus and its surrounding structures, mouth including all interior mouth structures such as tongue (entire area of tongue to include anterior, posterior, dorsal, ventral, and sublingual), floor of mouth including arterial and nerve beds, linea alba, buccal mucosa, buccal flanges, lingual flanges, nose, interior of nose (epithelial lining), all muscles of the tongue and surrounding the tongue, all arterial, venous and nerve beds of the tongue and surrounding the tongue, all glands and tissue of the head and neck and any other structure of the head and neck.

RF and/or Laser Assisted Vaginal Wound Repair:
1. Drink 4 oz. diluted Substrate 1;
2. Wait 15 minutes;
3. Drink 4 oz. diluted Substrate 2;
4. Wait 15 minutes;
5. Direct RF/laser, RF or laser energy at the vagina and its surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, and epithelium.

RF and/or Laser Assisted Anal Wound Repair:
1. Drink 4 oz. diluted Substrate 1;
2. Wait 15 minutes;
3. Drink 4 oz. diluted Substrate 2;
4. Wait 15 minutes;
5. Direct RF/laser, RF or laser energy at the anus and its surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, and epithelium.

RF and/or Laser Assisted Breast Wound Repair/Tissue Generation:
1. Drink 4 oz. diluted Substrate 1;
2. Wait 15 minutes;
3. Drink 4 oz. diluted Substrate 2;
4. Wait 15 minutes;
5. Direct RF/laser, RF or laser energy at the breast and its surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, lymph nodes and epithelium.

RF and/or Laser Assisted Tongue Wound Repair:
1. Drink 4 oz. diluted Substrate 1;
2. Wait 15 minutes;
3. Drink 4 oz. diluted Substrate 2;
4. Wait 15 minutes;
5. Direct RF/laser, RF or laser energy at tongue and its surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, and epithelium.

RF and/or Laser Assisted Skin and Tissue Wound Repair:
1. Drink 4 oz. diluted Substrate 1;
2. Wait 15 minutes;
3. Drink 4 oz. diluted Substrate 2;
4. Wait 15 minutes;
5. Direct RF/laser, RF or laser energy at skin and tissue and their surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, and epithelium.

RF and/or Laser Assisted Pore Repair:
1. Drink 4 oz. diluted Substrate 1;
2. Wait 15 minutes;
3. Drink 4 oz. diluted Substrate 2;
4. Wait 15 minutes;
5. Direct RF/laser, RF or laser energy at pores and their surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, and epithelium.

RF and/or Laser Assisted Oral Cavity Wound Repair:
1. Drink 4 oz. diluted Substrate 1;
2. Wait 15 minutes;
3. Drink 4 oz. diluted Substrate 2;
4. Wait 15 minutes;
5. Direct RF/laser, RF or laser energy at oral cavity and its' surrounding structures;
6. Keep energy in place for 10-20 minutes or until desired effect achieved;
7. Rotate hand piece; and
8. Repeat steps 5-7 until desired result achieved.

Surrounding structures include, but are not limited to, all bone, cartilage, muscles, tendons, nerves, blood vessels, and epithelium.

Further still, wound treatment may be utilized for additional conditions including, but not limited to, vaginal wound repair, breast wound repair/regeneration/generation, anal wound repair, age spot repair, pore repair, skin and tissue repair and general body wound repair.

EXAMPLES

I. Analysis of Tooth #15 at 12 Unique Loci

A patient's pocket depths at tooth 15 were measured at 12 separate loci. The root of the tooth was then scaled and planed to remove calculus build up on the root surface. After scaling and planning, bleeding occurs in the sulcus. The sulcus was allowed to air dry and immediately thereafter the conditioner is applied to the sulcus and left for 30 seconds before being rinsed with saline. The tooth was next scaled and planed again to renew blood flow. With blood pooling in the sulcus, the 45° laser tip was placed into the sulcus. The laser light used has a wavelength in the visible portion of the electromagnetic spectrum, between 400 nm-700 nm wavelength. The laser was emitted continuously with only intermittent stops for tissue temperature control. The laser was allowed to penetrate the entire sulcus by moving the tip vertically and horizontally throughout the sulcus for 30 second. The laser tip was cut to 45° in the opposite angle for the second pass into the sulcus and 90° for the third pass to allow the laser bean to penetrate the existing periodontium to decontaminate and biostimulate the sulcular contents.

In the meantime, the first substrate and the second substrate were mixed in a glass dish. Some of the patient's blood that has been treated with the laser light in the sulcus was also mixed in the glass dish. This mixture is then placed immediately into the sulcus upon mixture. Enough of the mixture was placed into the sulcus to fill the sulcus while ensuring the mixture stayed 3 mm below the top of the gingival margin and also remained immersed in blood. The patient's mouth was kept open for 5 minutes to ensure the newly formed blood clot containing the substrate mixture remained intact.

Figure 11:
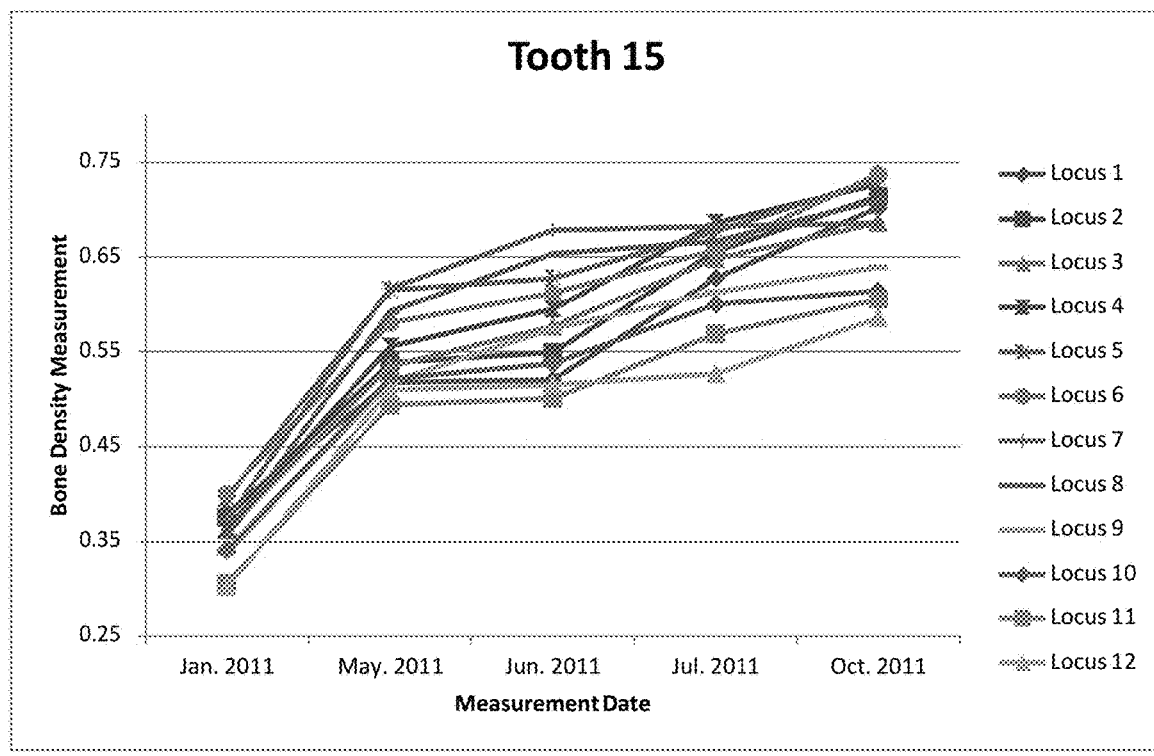
FIG. 11 shows bone density measurements for tooth 15 of a patient at 12 loci on the tooth following treatment with a soft tissue diode laser and a substrate over time.

Treatment was repeated on tooth 15 on four subsequent occasions, at which time the pocket depths at each loci were measured prior to treatment. Measurements are shown in FIG. 11. The data show an increase in calcium density at the specific loci.

II. Analysis of Tooth #12 at 17 Unique Loci

Figure 12:
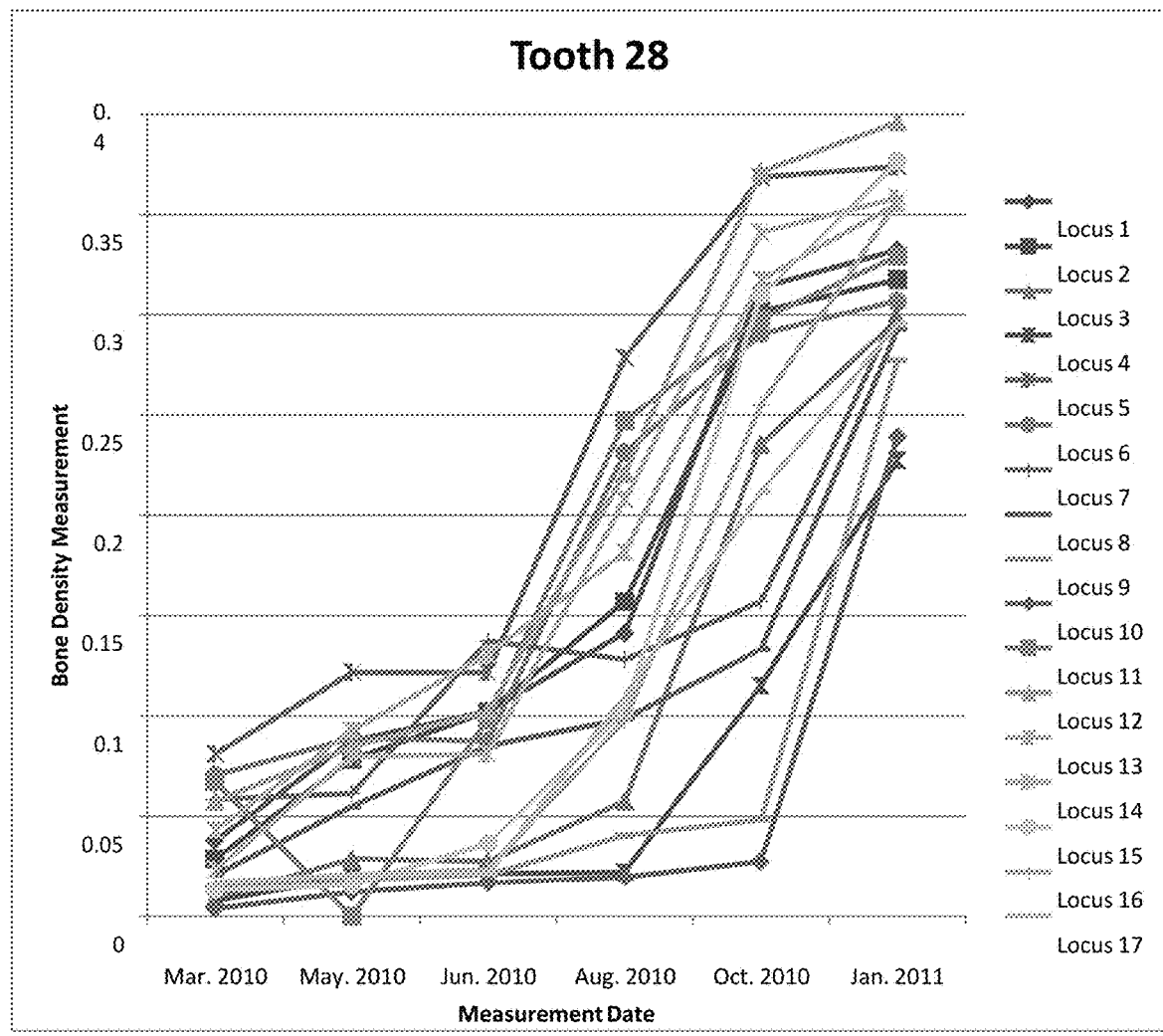
FIG. 12 shows bone density measurements for tooth 28 of a patient at 17 loci on the tooth following treatment with a soft tissue diode laser and a substrate over time.

A patient's pocket depths at tooth 28 were measured at 17 separate loci. The treatment disclosed herein was performed on five subsequent occasions, at which time the pocket depths at each loci were measured prior to treatment. Measurements are shown in FIG. 12. The data show an increase in calcium density across all loci.

III. Analysis of Tooth #2, #3 and #15 at 3 Unique Loci Per Tooth

Figure 13:
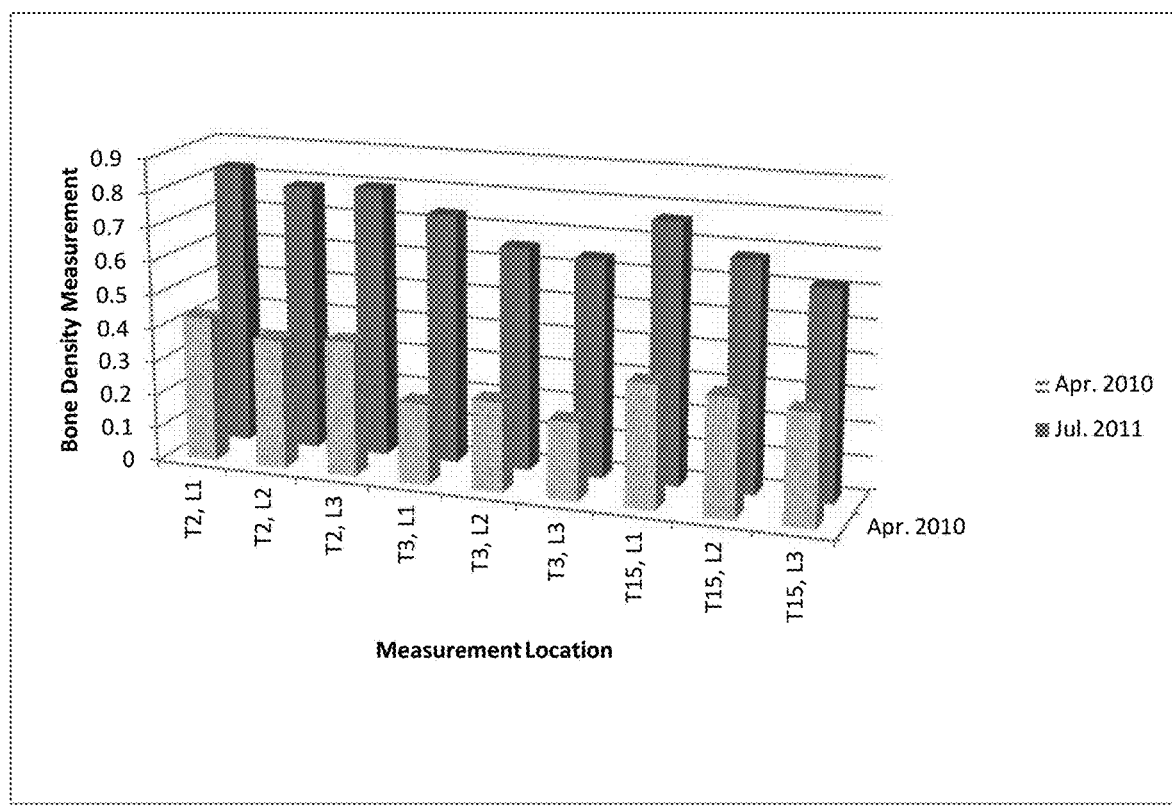
FIG. 13 shows bone density measurements for tooth 2, tooth 3 and tooth 15 of a patient at 3 loci per tooth following treatment with a soft tissue diode laser and a substrate over time.
Figure 14A:
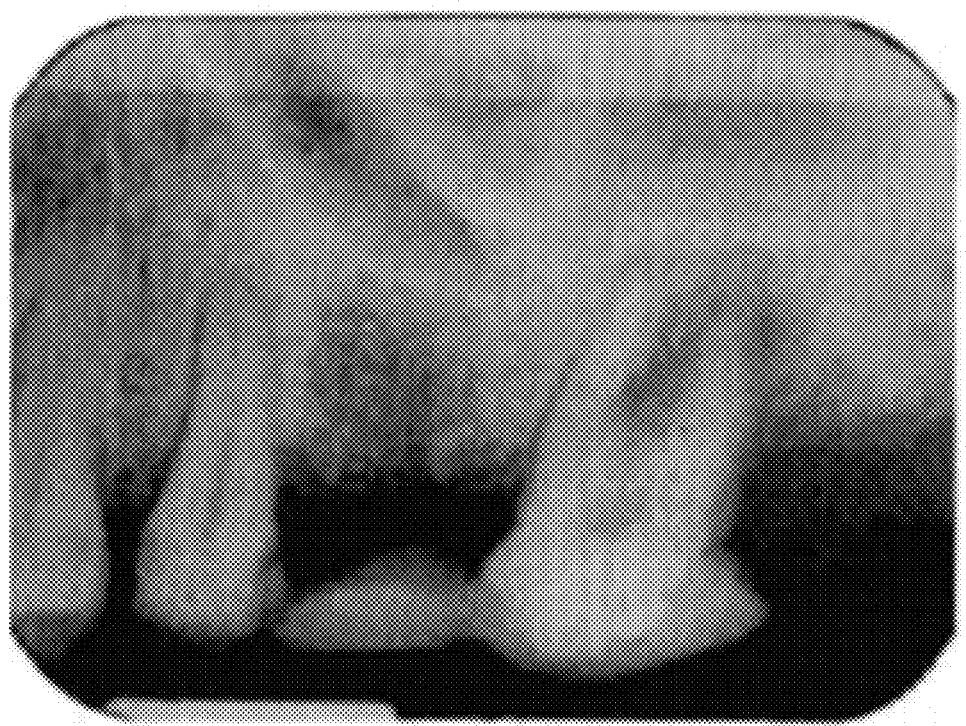
FIGS. 14a and 14b show X-rays of tooth 15 of a patient from which measurements shown in FIG. 11 were collected. (a) shows tooth 15 before treatment. (b) shows tooth 15 at the October 2011 measurement following three treatments.
Figure 14B:
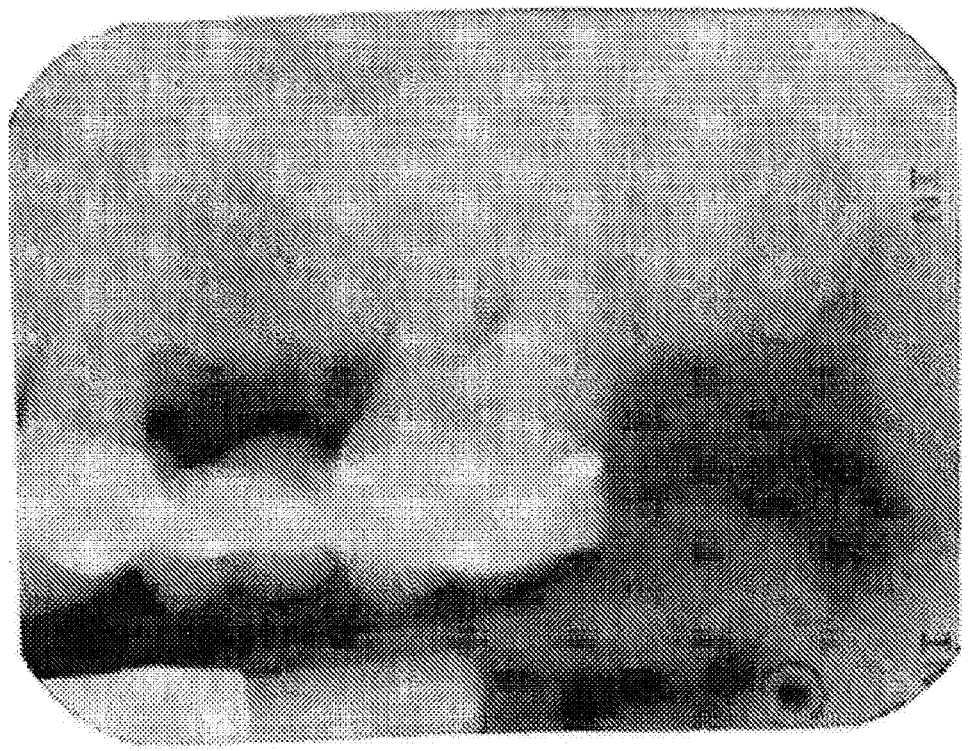
Figure 15A:
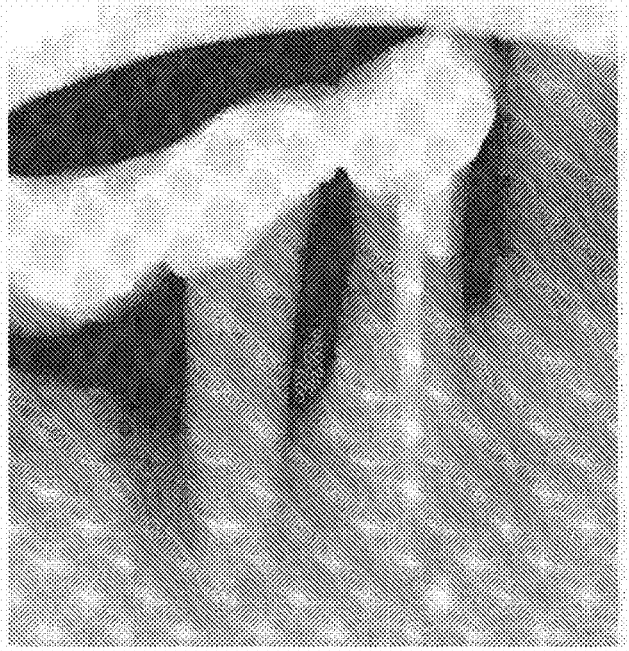
FIGS. 15a and 15b show X-rays of tooth 28 of a patient from which measurements shown in FIG. 12 were collected. (a) shows tooth 28 before treatment. (b) shows tooth 28 at the January 2011 measurement following four treatments.
Figure 15B:
Figure 16A:
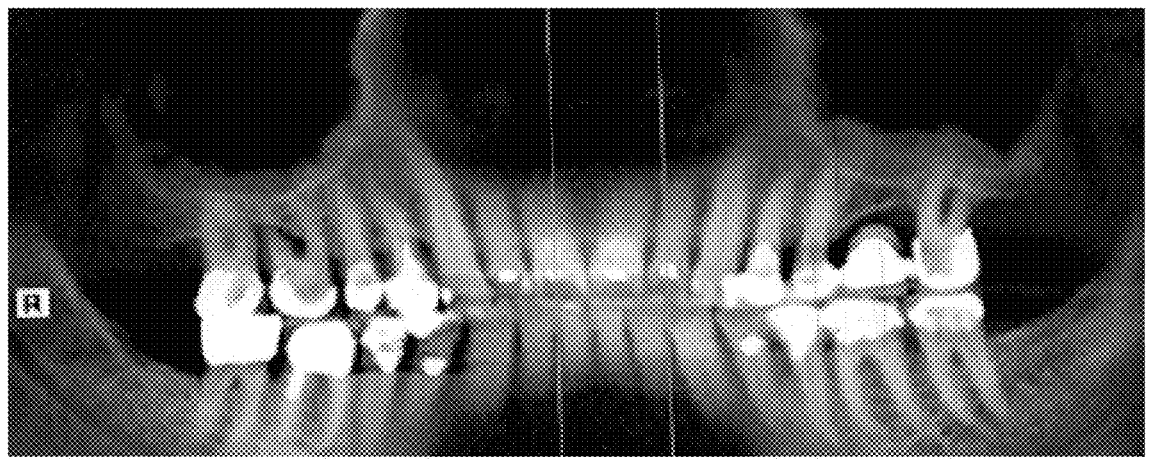
FIGS. 16a and 16b show a panoramic X-ray of tooth 2, tooth 3 and tooth 15 of a patient from which measurements shown in FIG. 13 were collected. (a) shows the teeth before treatment. (b) shows the teeth at the July 2011 measurement.
Figure 16B:

A patient's pocket depths at tooth 2, tooth 3 and tooth 15 were measured at three separate loci per tooth. The treatment disclosed herein was performed 3 months after the initial treatment, at which time the pocket depths at each loci were measured prior to treatment. Measurements are shown in FIG. 13. The data show a progression of bone generation.

IV. Analysis of Chin Profile

Figure 24:
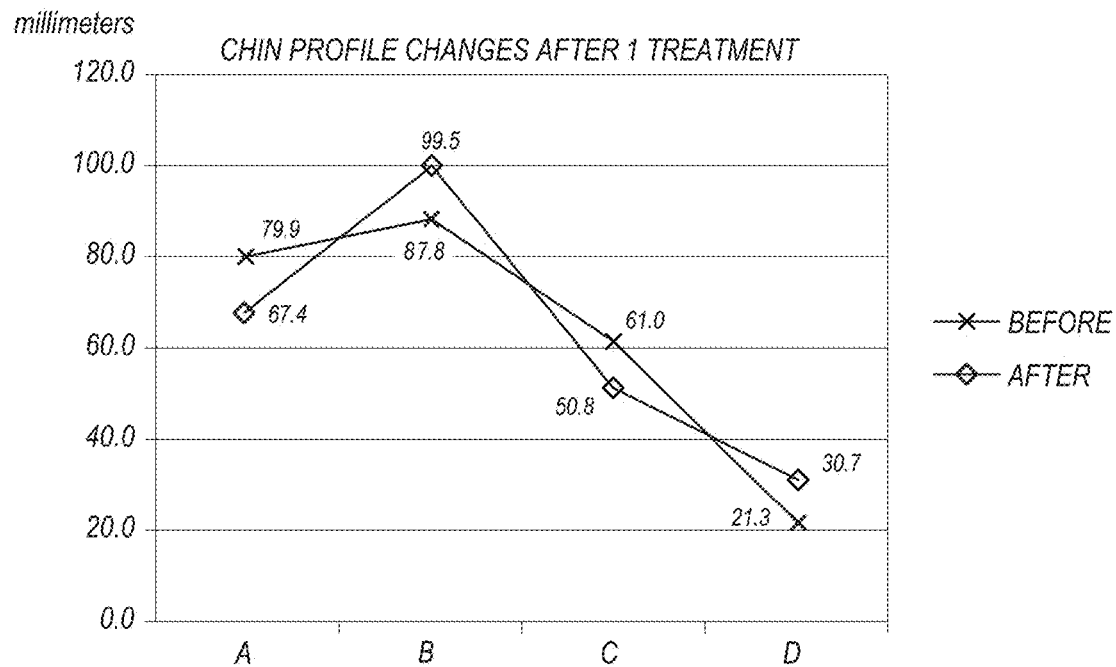
FIG. 24 shows chin profile measurements before and after treatment.

A patient's chin profile was measured. The treatment disclosed herein was performed once after the initial measurements were taken with measurements repeated following treatment. Measurements are shown in FIG. 24. The data show a general increase in chin profile following a single treatment.

V. Analysis of Toe Crease

Figure 25:
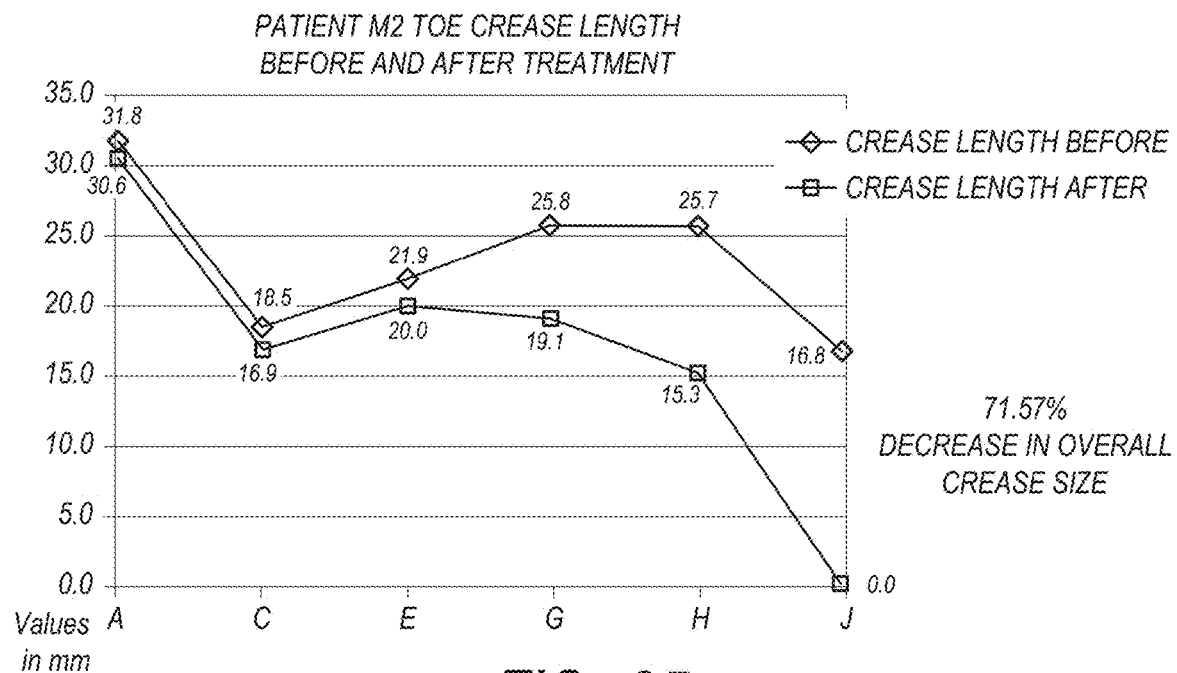
FIG. 25 shows toe crease length measurements before and after treatment.

A patient's toe crease length was measured. The treatment disclosed herein was performed after initial measurements were obtained with measurements repeated following treatment. Measurements are shown in FIG. 25. The data show a 71% overall decrease in crease size following treatment.

VI. Analysis of Gingival Wound Tissue

A patient's gingival wounds were measured from the line to the top of the gingiva. The treatment disclosed herein was performed and measurements were repeated following treatment. Images of gingival wounds are shown before and after treatment in FIGS. 26*a* and 26*b*. Measurements are shown in FIG. 26c. The data show a 50% or greater decrease in the wound following a single treatment.

VII. Analysis of Hand Crease

Figure 27:
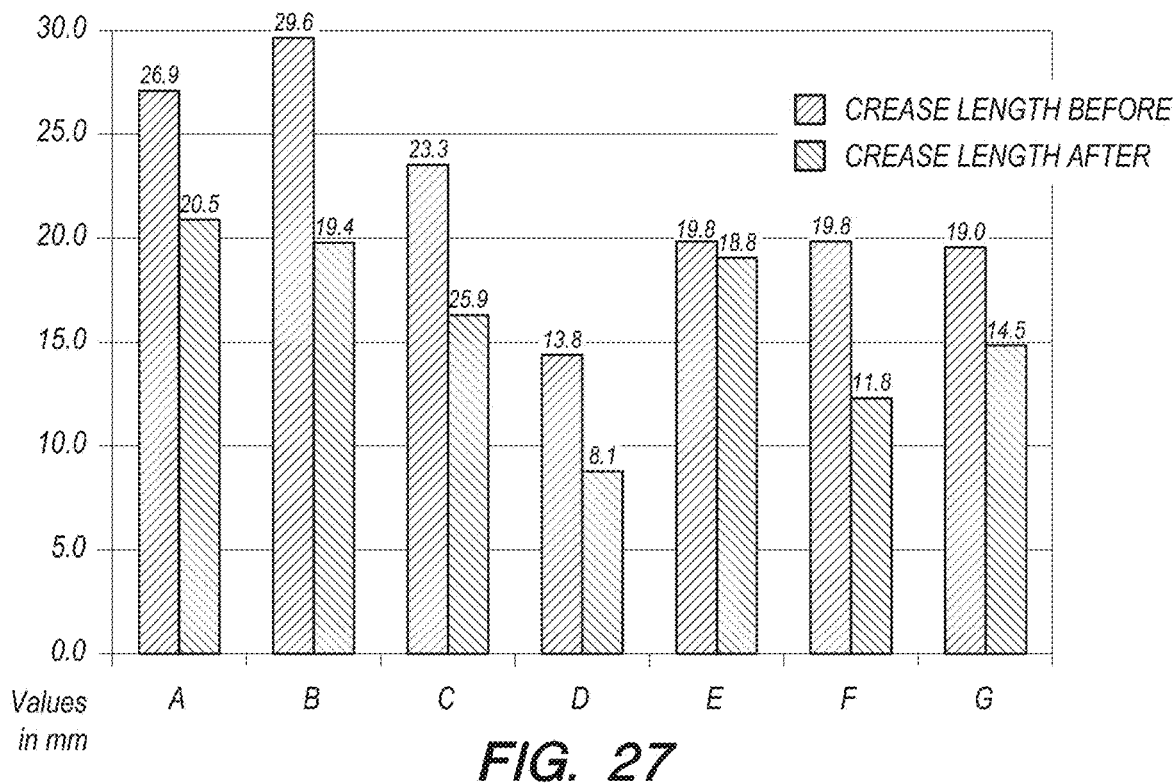
FIG. 27 shows hand crease length measurements before and after treatment.

A patient's hand crease length was measured. The treatment disclosed herein was performed after initial measurements were taken with measurements repeated following treatment. Measurements are shown in FIG. 27. The data show an overall decrease in crease length following treatment.

VIII. Analysis of New Skin Growth

Figure 28:
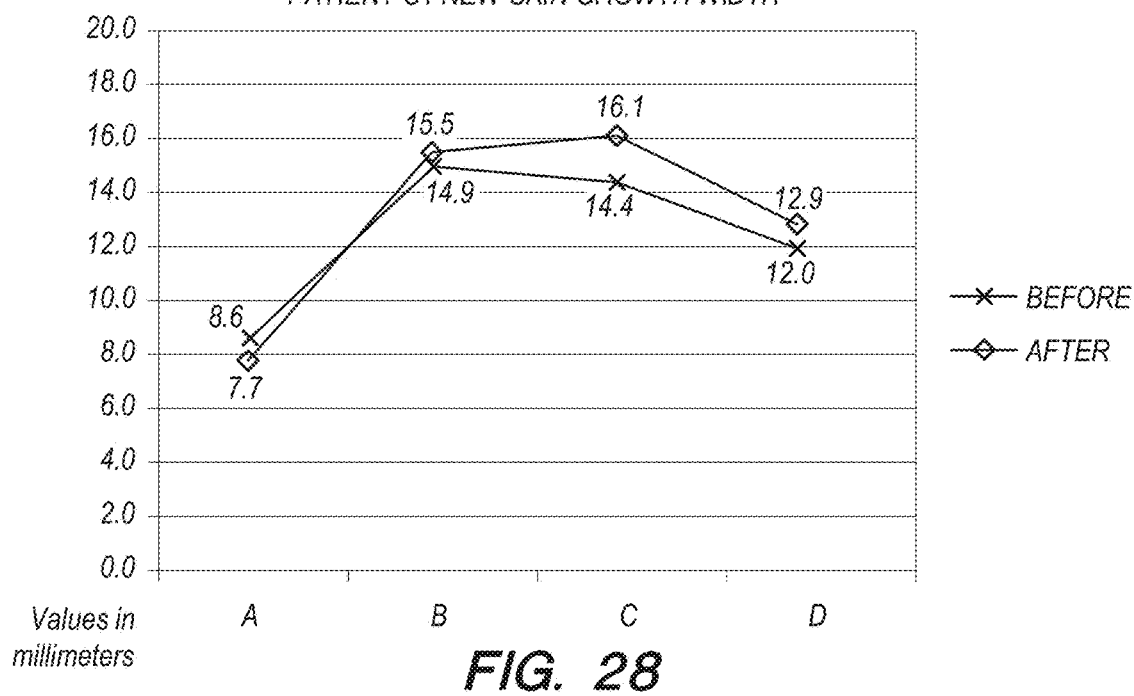
FIG. 28 shows wound new skin growth measurements before and after treatment.

A patient's skin leg wound was measured. The treatment disclosed herein was performed after initial measurements were taken with measurements repeated following treatment. Measurements are shown in FIG. 28. The data show an overall increase in new skin growth following treatment.

IX. Analysis of Anal Scar Reduction

Figure 29:
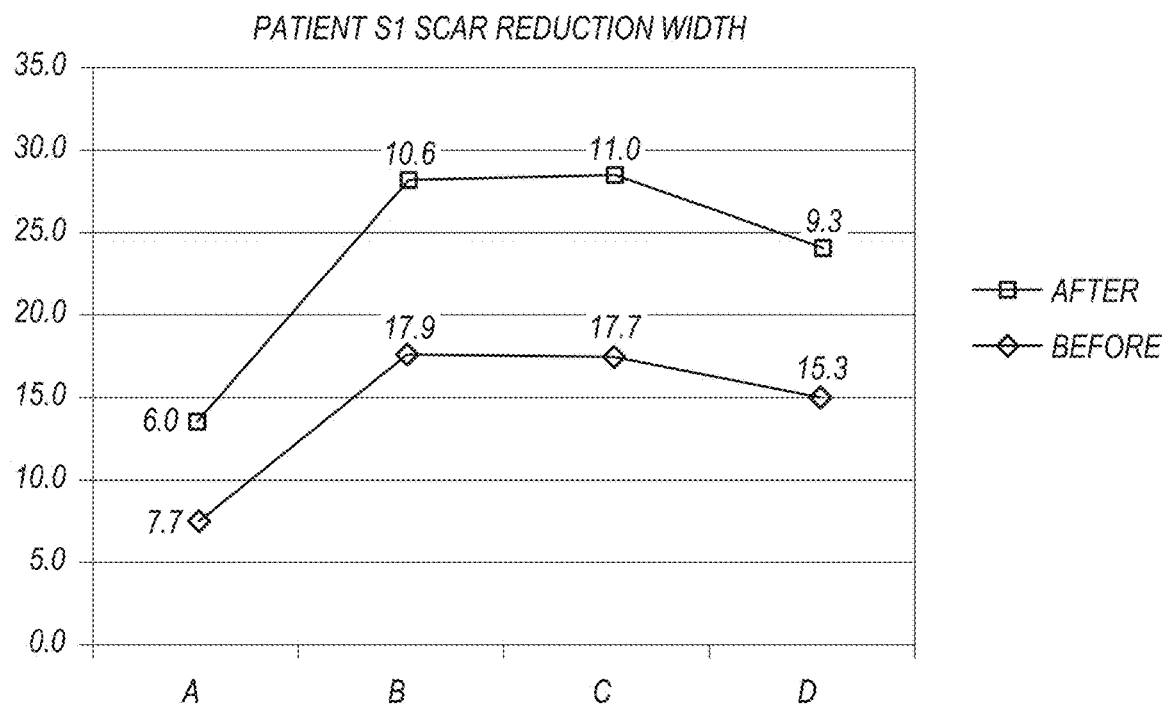
FIG. 29 shows (anal) scar width reduction measurements before and after treatment.
Figure 30:
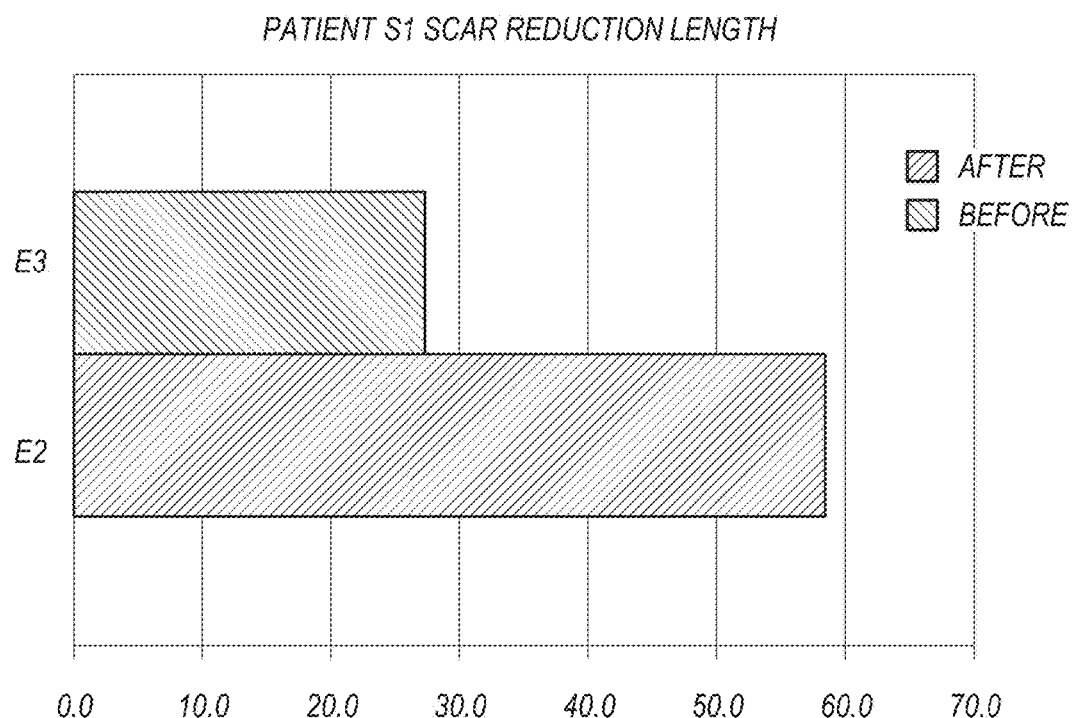
FIG. 30 shows (anal) scar length reduction measurements before and after treatment.

A patient's anal scar tissue was measured. The treatment disclosed herein was performed after initial measurements were taken with measurements repeated following treatment. Measurements are shown in FIG. 29 and FIG. 30. The data show a reduction in both length and width of scar tissue following treatment.

X. Analysis of Tongue Strength

Figure 31:
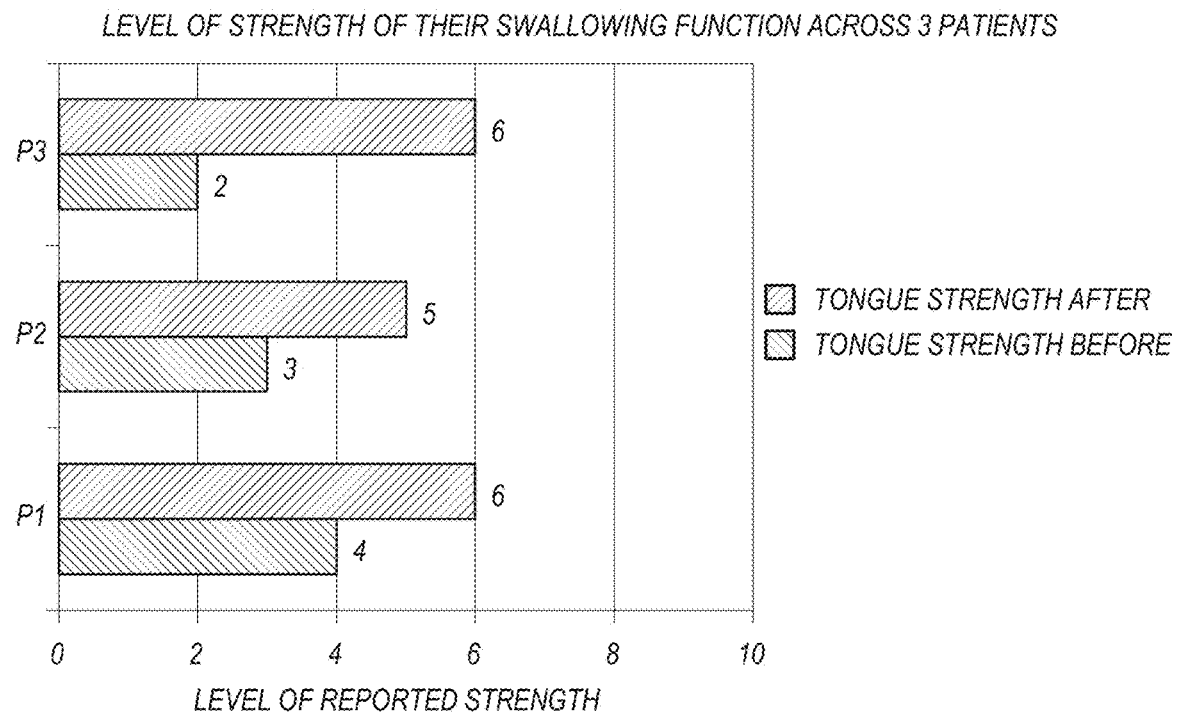
FIG. 31 shows swallowing strength measurements before and after treatment.

Tongue strength and swallowing was assessed for three patients. The treatment disclosed herein was performed after initial assessments were made and tongue strength and swallowing were reevaluated following treatment. Measurements are shown in FIG. 31. The data show each patient experiencing an increase in tongue strength following treatment.

XI. Analysis of Breast Firmness

Figure 32:
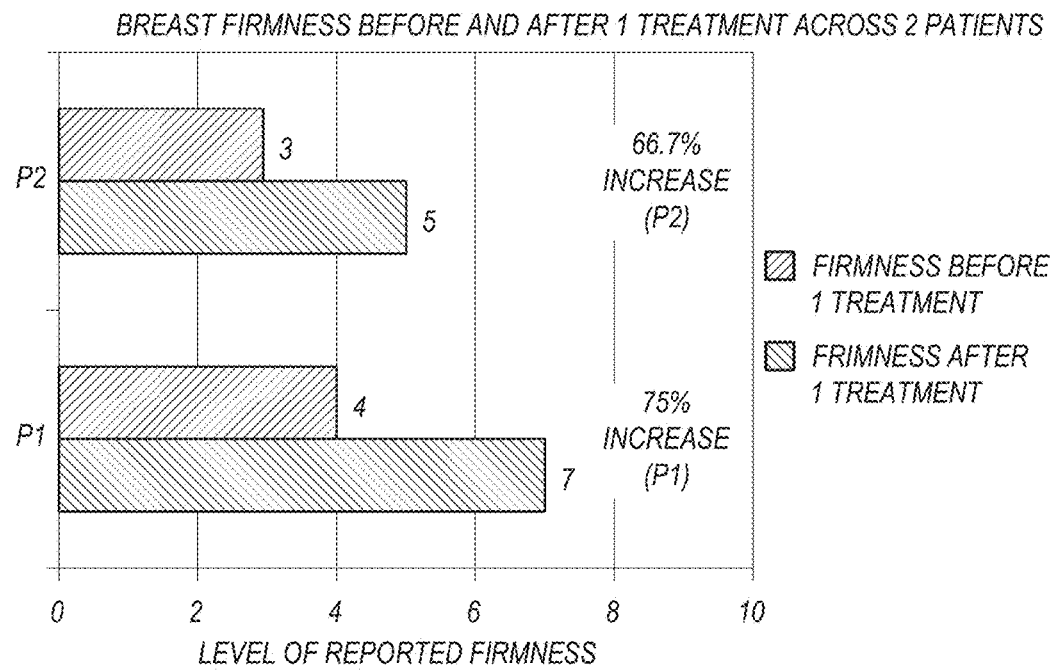
FIG. 32 shows breast firmness measurements before and after treatment.

Breast firmness was recorded for two patients. The treatment disclosed herein was performed after initial assessments were made and breast firmness was reevaluated following treatment. Comparative firmness is shown in FIG. 32. The data show the patients experiencing an increase in firmness of 75% and 66.7% following treatment, respectively.

One embodiment of the present invention provides a device for treating a wound according to the method described herein, the device emitting a laser a beam of light having a wavelength in the green wavelength range (520-570 nm), red wavelength range (620-750 nm), or yellow wavelength range (570-590 nm) having an alternative wattage of 0.001 W to 5 W, preferably 0.002 W to 4 W, more preferably 0.003 W to 3 W, and most preferably 0.005 W to 2 W.

Another embodiment of the present invention provides a device for treating a wound according to the method described herein, the device emitting a RF beam up to 10 W comprised of a carrier wave frequency in the range of 0.1 MHz to 20 MHz and a non-sinusoidal waveform in the range of 0 to 40 KHz. In a preferred embodiment, the carrier wave frequency is in the range of 0.2 MHz to 10 MHz, preferably 0.3 MHz to 5 MHz. Optionally a 0.001 W to 10 W range RF energy, preferably a 0.001 W to 3 W range, is utilized in the hertz range of 40 Hz to 24 GHz. In a further alternative embodiment, the RF wave is more than one sine wave wherein the more than one demonstrates a harmonics pattern.

Yet another embodiment of the present invention provides a device for treatment of a wound according to the method described herein, the device emitting a laser beam, a RF beam or a combination thereof.

Still another embodiment of the present invention provides a device for treatment of wounds in the oral cavity according to the method described herein, the device emitting a fiber optic laser beam. In a preferred embodiment, the fiber optic device may be used in conjunction with the laser and RF device for treating wounds of the oral cavity.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed.

Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

The invention claimed is:

1. A device for treatment of wounds on an individual, the device comprising:
   a first energy source configured for biostimulating soft tissue and controlling a temperature of the tissue to prevent tissue welding, wherein the first energy source comprises an energy waveform having a wattage of 0.001 W to 3 W and a frequency of 40 Hz to 20 kHz,
   a second energy source also configured for biostimulating the soft tissue and controlling the temperature of the tissue to prevent tissue welding configured to be used together with the first energy source, wherein the second energy source is a laser light having a wavelength in the visible portion of the electromagnetic spectrum between 400 nm-700 nm wavelength, and
   a hand piece having one or more tips or openings through which the waveform and the laser light exits,
   wherein the waveform having the wattage of 0.001 W to 3 W and frequency of 40 Hz to 20 KHz from the first energy source, and the light having the wavelength between 400 nm-700 nm from the second energy source, are configured to cause tissue regeneration, and avoid tissue damage, without loss of tissue volume, in a wound when delivered together to the wound through the one or more tips or openings in the hand piece; and
   wherein the light and/or waveform is configured to be placed over the wound using the hand piece, the wound located at a non-epidermal wound site comprising a periodontal pocket, a periodontium, a bone, or a sulcus.

2. The device of claim 1, wherein the wavelength is selected from a group consisting of a green wavelength range (520-570 nm), a red wavelength range (620-700 nm) and a yellow wavelength range (570-590 nm).

3. The device of claim 2, wherein laser light with a wavelength of 660 nm has a wattage of 0.003 W to 0.089 W; and laser light with other wavelengths has a wattage of 0.003 W to 3 W or 0.005 W to 2 W.

4. A device for treatment of wounds on an individual, the device comprising:
  first and second energy sources, wherein the first and second energy sources are configured to be used together for biostimulating soft tissue and controlling a temperature of the tissue to prevent tissue welding,
    the first energy source comprising a laser light having a wavelength in the visible portion of the electromagnetic spectrum between 400 nm-700 nm wavelength and a wattage of 0.003 W to 3 W,
    the second energy source comprising an energy waveform having a wattage of 0.001 W to 3 W and frequency of 40 Hz to 20 kHz, and
  a hand piece having a tip through which the laser light and the waveform exits,
  wherein the waveform having the wattage of 0.001 W to 3 W and frequency of 40 Hz to 20 KHz, and the light having the wavelength between 400 nm-700 nm and the wattage of 0.003 W to 3 W, are configured to cause tissue regeneration, and avoid tissue damage, without loss of tissue volume, in a wound when delivered together to the wound through the tip of the hand piece, and
  wherein the light and/or waveform is configured to be placed over the wound using the hand piece, the wound located at a non-epidermal wound site comprising a periodontal pocket, a periodontium, a bone, or a sulcus.

5. The device of claim 1, wherein the first energy source comprises a waveform having a wattage of 0.001 W to 3 W, and the frequency range of 40 Hz to 20 KHz, wherein the waveform is configured to be used independently of any other energy source.

6. A device for treatment of wounds on an individual, the device comprising:
  first and second energy sources configured to be used together for biostimulating soft tissue and controlling a temperature of the tissue to prevent tissue welding, wherein the first energy source comprises an energy wave having a wattage of 0.001 W to 3 W and frequency of 40 Hz to 20 KHz, and the second energy source comprises a laser light wave,
  wherein the energy wave, and the laser light wave, are configured to cause tissue regeneration, and avoid tissue damage, without loss of tissue volume, in a wound when delivered together to the wound.

7. The device of claim 6, wherein the energy wave comprises a square wave.

8. The device of claim 6, wherein the first energy source comprises a waveform having a wattage of 0.001 W to 3 W and the frequency range of 40 Hz to 20 KHz, wherein the waveform is configured to be used independently of any other energy source.

\* \* \* \* \*